(12) United States Patent
Kealey et al.

(10) Patent No.: US 11,399,841 B2
(45) Date of Patent: Aug. 2, 2022

(54) THIN-FILM MICROMESH MEDICAL DEVICES AND RELATED METHODS

(71) Applicant: Monarch Biosciences, Inc., Los Angeles, CA (US)

(72) Inventors: Colin Kealey, Los Angeles, CA (US); Ian A. Cook, Los Angeles, CA (US); Vikas Gupta, Los Angeles, CA (US)

(73) Assignee: MONARCH BIOSCIENCES, INC., Los Angeles, CA (US)

( * ) Notice: Subject to any disclaimer, the term of this patent is extended or adjusted under 35 U.S.C. 154(b) by 0 days.

(21) Appl. No.: 15/615,698

(22) Filed: Jun. 6, 2017

(65) Prior Publication Data

US 2017/0265870 A1    Sep. 21, 2017

Related U.S. Application Data

(63) Continuation of application No. PCT/US2016/040864, filed on Jul. 1, 2016.
(Continued)

(51) Int. Cl.
*A61F 2/91*    (2013.01)
*A61L 31/02*    (2006.01)
(Continued)

(52) U.S. Cl.
CPC .. *A61B 17/12118* (2013.01); *A61B 17/12168* (2013.01); *A61F 2/856* (2013.01);
(Continued)

(58) Field of Classification Search
None
See application file for complete search history.

(56) References Cited

U.S. PATENT DOCUMENTS 6,312,463 B1    11/2001  Rourke et al.
6,666,882 B1    12/2003  Bose et al.
(Continued)

FOREIGN PATENT DOCUMENTS

WO    WO 2011/150118    12/2011
WO    WO 2014/131037    8/2014
(Continued)

OTHER PUBLICATIONS

PCT International Search Report and Written Opinion of International Application No. PCT/US2016/040864, 12 pages, dated Nov. 29, 2016.
(Continued)

*Primary Examiner* — Leslie Lopez
(74) *Attorney, Agent, or Firm* — Haynes and Boone, LLP

(57) ABSTRACT

Thin-film mesh for medical devices, including stent and scaffold devices, and related methods are provided. Micropatterned thin-film mesh, such as thin-film Nitinol (TFN) mesh, may be fabricated via sputter deposition on a micropatterned wafer. The thin-film mesh may include slits to be expanded into pores, and the expanded thin-film mesh used as a cover for a stent device. The stent device may include two stent modules that may be implanted at a bifurcated aneurysm such that one module passes through a medial surface of the other module. The thin-film mesh may include pores with complex, fractal, or fractal-like shapes. The thin-film mesh may be used as a scaffold for a scaffold device. The thin-film scaffold may be placed in a solution including structural protein such as fibrin, seeded with cells, and placed in the body to replace or repair tissue.

10 Claims, 29 Drawing Sheets

Related U.S. Application Data

(60) Provisional application No. 62/216,965, filed on Sep. 10, 2015, provisional application No. 62/209,254, filed on Aug. 24, 2015, provisional application No. 62/209,185, filed on Aug. 24, 2015, provisional application No. 62/188,218, filed on Jul. 2, 2015.

(51) Int. Cl.

| | | |
|---|---|---|
| *A61L 31/16* | (2006.01) | |
| *A61L 27/38* | (2006.01) | |
| *A61F 2/90* | (2013.01) | |
| *A61F 2/07* | (2013.01) | |
| *A61B 17/12* | (2006.01) | |
| *A61F 2/856* | (2013.01) | |
| *A61F 2/915* | (2013.01) | |
| *A61L 31/14* | (2006.01) | |
| *A61L 27/36* | (2006.01) | |
| *A61L 27/30* | (2006.01) | |
| *A61L 27/06* | (2006.01) | |
| *A61L 31/08* | (2006.01) | |
| *A61F 2/06* | (2013.01) | |
| *A61F 2/30* | (2006.01) | |

(52) U.S. Cl.
CPC .............. *A61F 2/90* (2013.01); *A61F 2/91* (2013.01); *A61F 2/915* (2013.01); *A61L 27/06* (2013.01); *A61L 27/306* (2013.01); *A61L 27/3695* (2013.01); *A61L 27/3804* (2013.01); *A61L 31/022* (2013.01); *A61L 31/088* (2013.01); *A61L 31/14* (2013.01); *A61L 31/16* (2013.01); *A61B 17/12177* (2013.01); *A61F 2/07* (2013.01); *A61F 2002/067* (2013.01); *A61F 2002/077* (2013.01); *A61F 2002/3006* (2013.01); *A61L 2300/64* (2013.01); *A61L 2400/16* (2013.01)

(56) References Cited

U.S. PATENT DOCUMENTS

| | | |
|---|---|---|
| 6,746,890 B2 | 6/2004 | Gupta et al. |
| 7,311,727 B2 | 12/2007 | Mazumder et al. |
| 2005/0070989 A1* | 3/2005 | Lye .................. A61F 2/91 623/1.4 |
| 2005/0186241 A1* | 8/2005 | Boyle .................. A61B 5/076 424/423 |
| 2007/0173787 A1* | 7/2007 | Huang .................. A61F 2/82 604/891.1 |
| 2007/0276469 A1 | 11/2007 | Tenne |
| 2008/0004653 A1 | 1/2008 | Sherman et al. |
| 2010/0063582 A1* | 3/2010 | Rudakov .......... A61B 17/12118 623/1.16 |
| 2012/0245706 A1 | 9/2012 | Alavi et al. |
| 2018/0110637 A1 | 4/2018 | Kealey et al. |

FOREIGN PATENT DOCUMENTS

| | | |
|---|---|---|
| WO | WO 2015/061496 | 4/2015 |
| WO | WO 2016/168765 | 10/2016 |
| WO | WO 2016/210380 | 12/2016 |

OTHER PUBLICATIONS

Gerullis, Holger et al., "Coating with Autologous Plasma Improves Biocompatibility of Mesh Grafts In Vitro: Development State of Surgical Innovation", BioMed Research International, vol. 2013, Jan. 1, 2013, pp. 1-6.

* cited by examiner

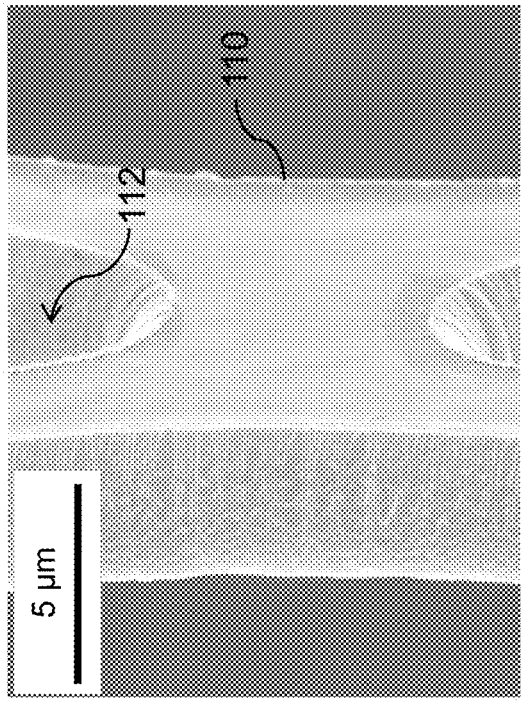
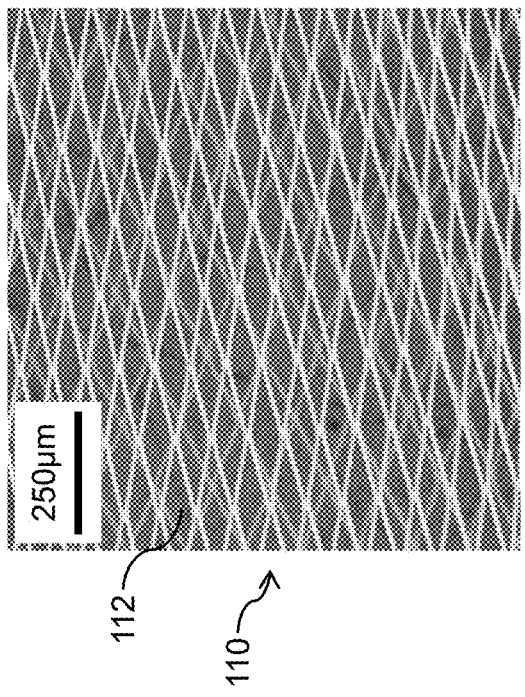
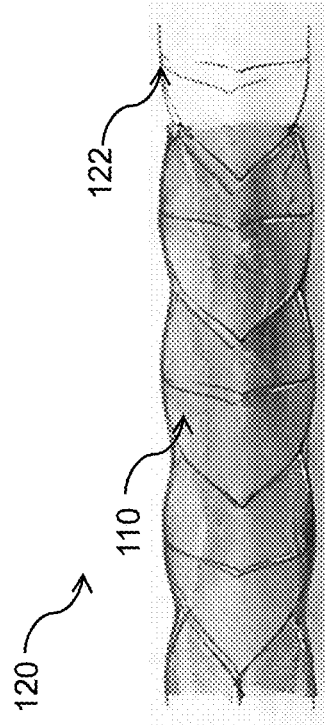
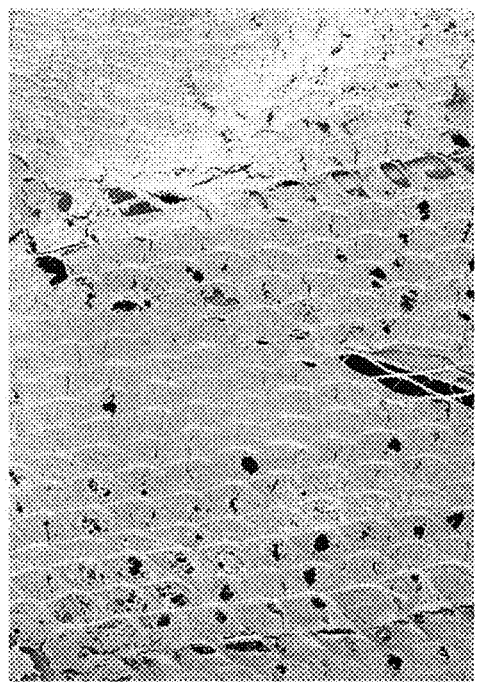
FIG. 2A
FIG. 2B
FIG. 2C
FIG. 2D

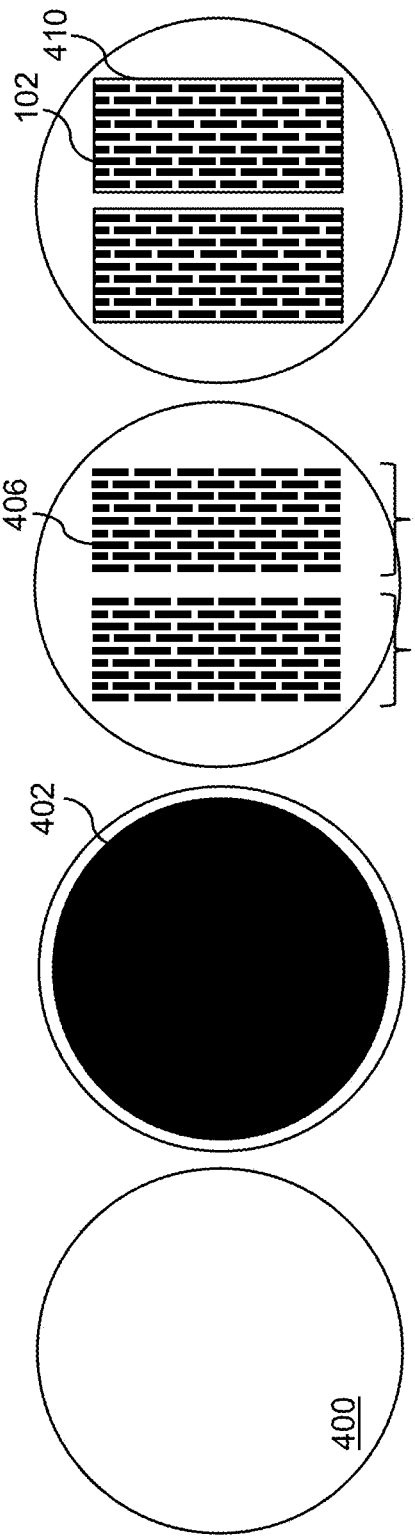
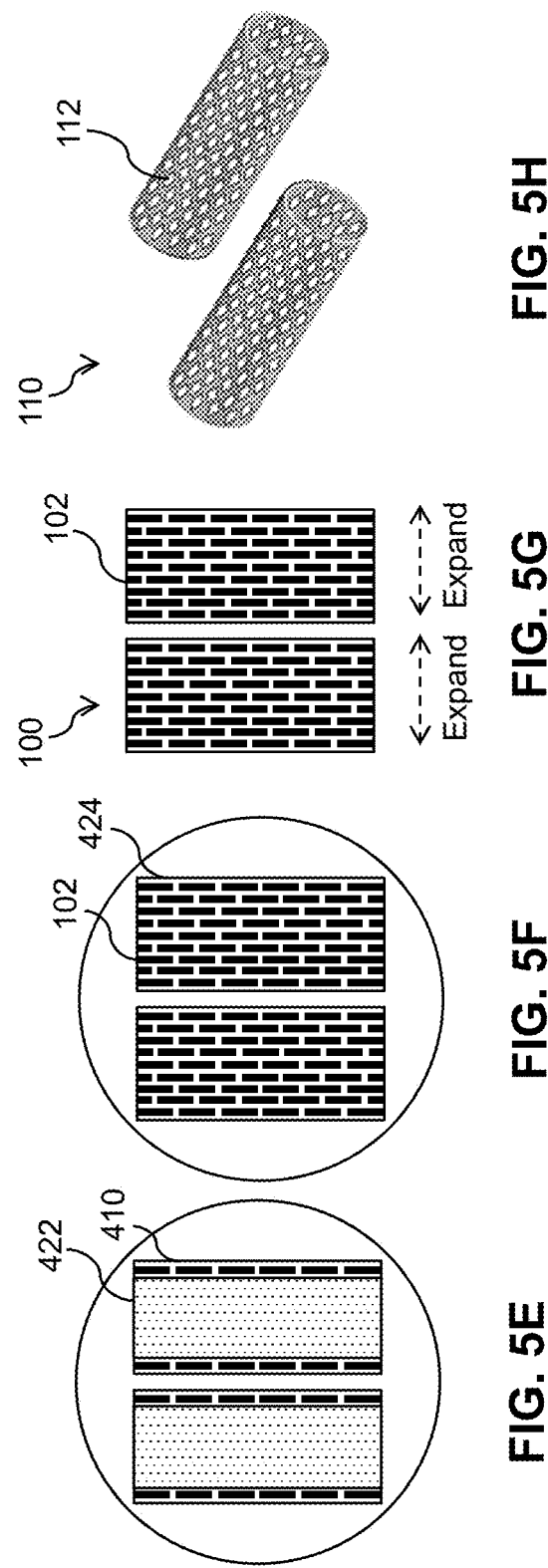

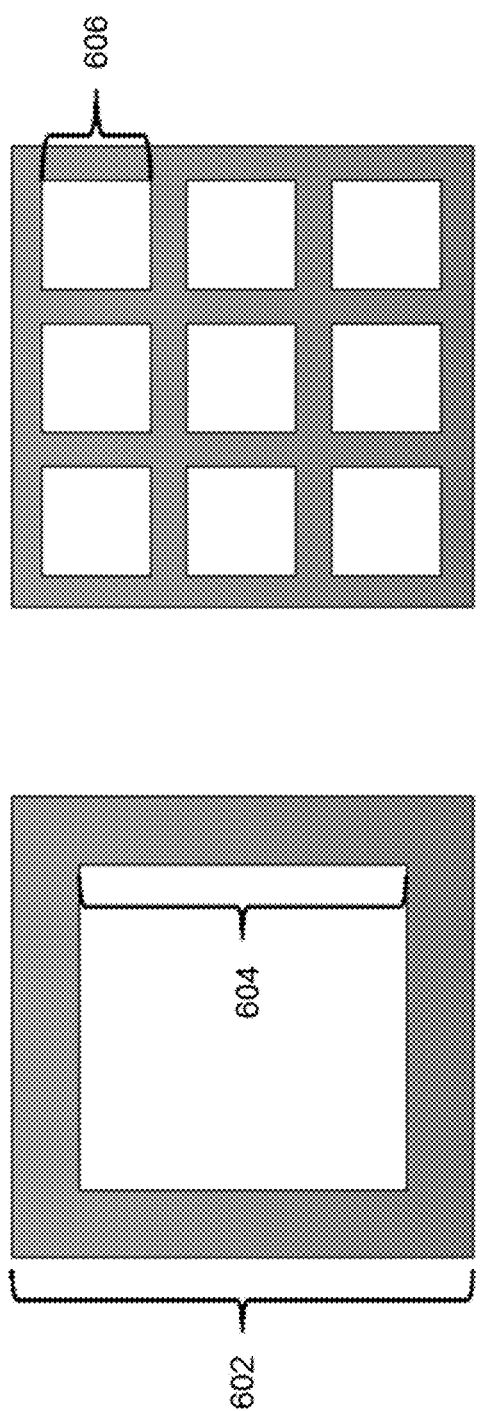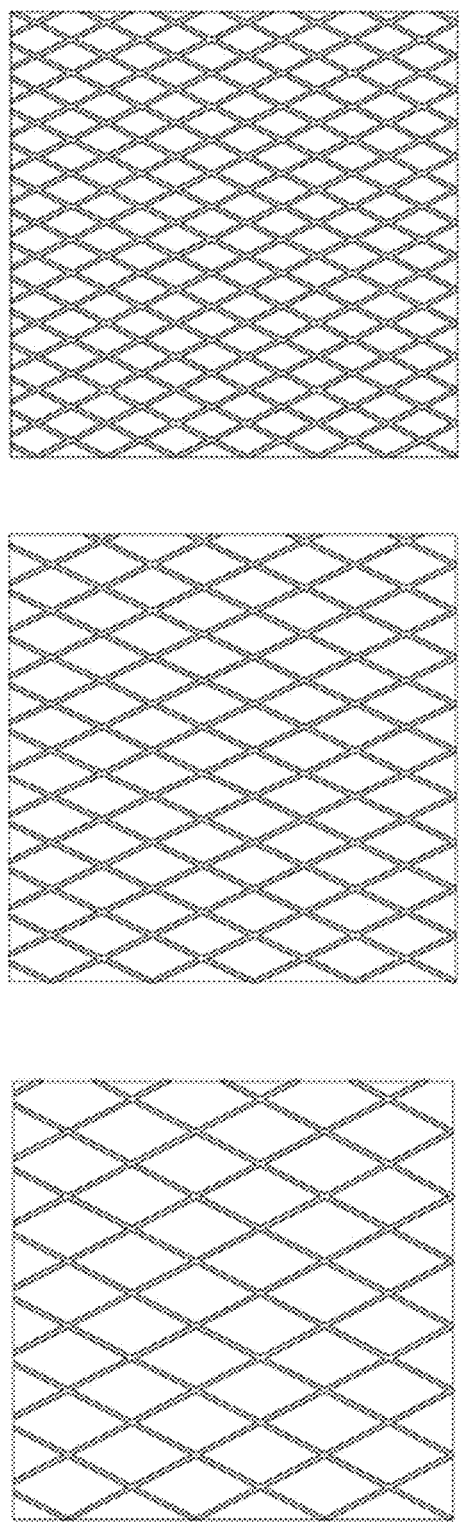

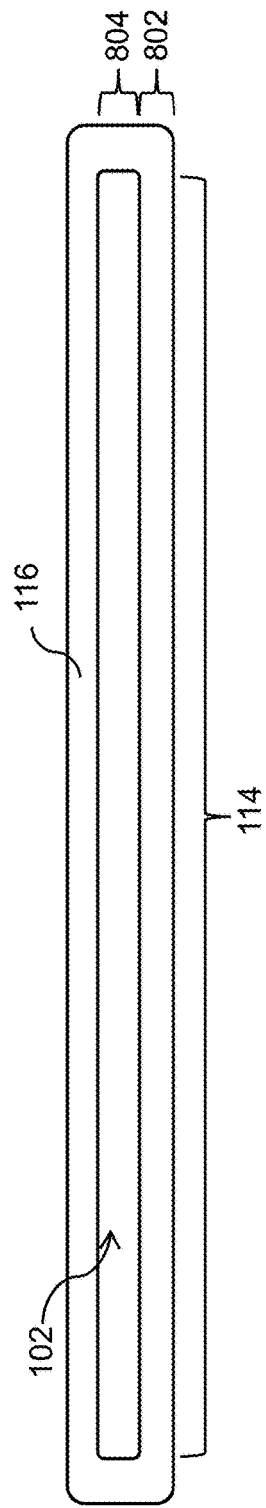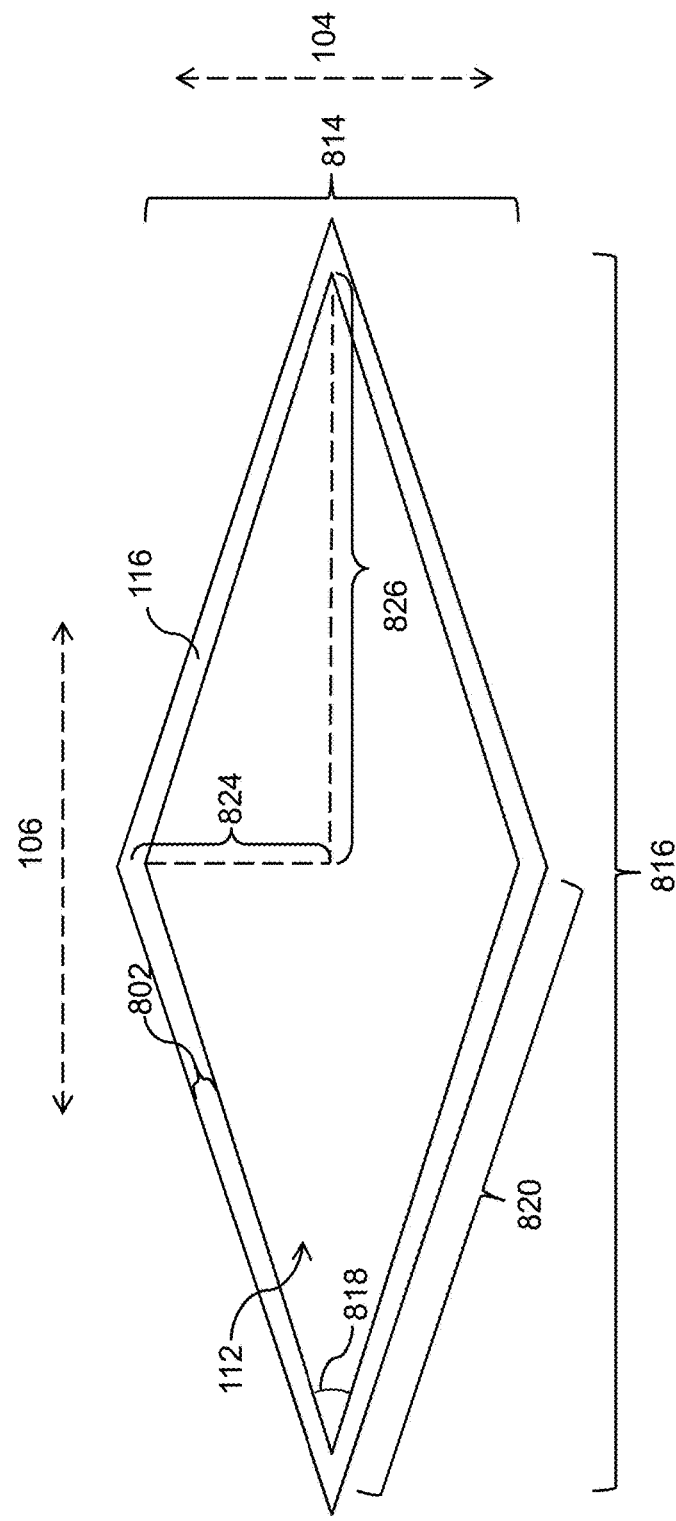

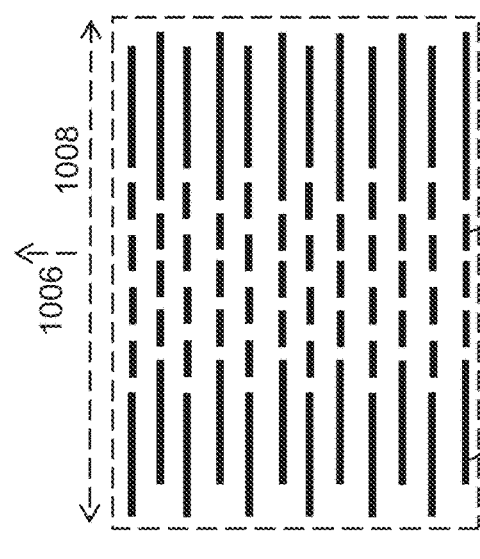
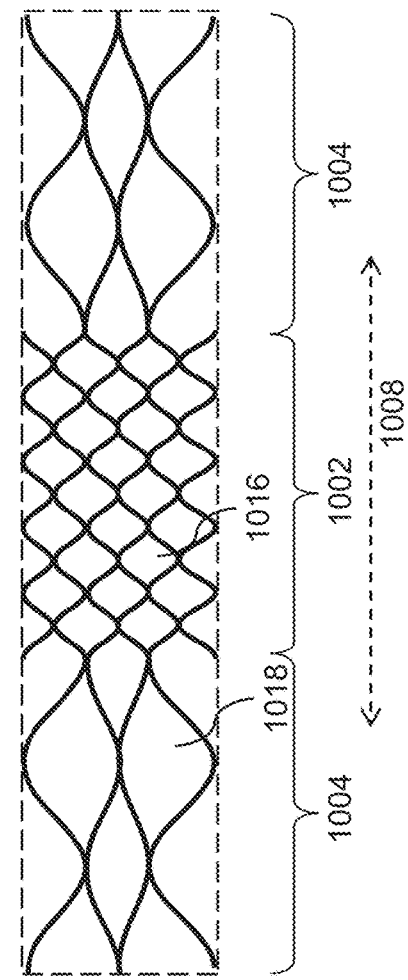

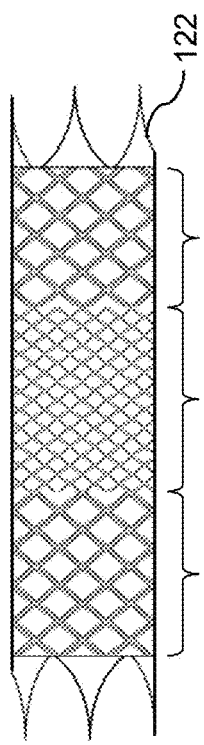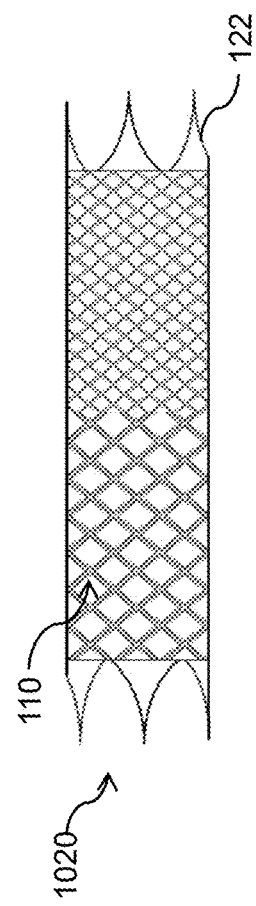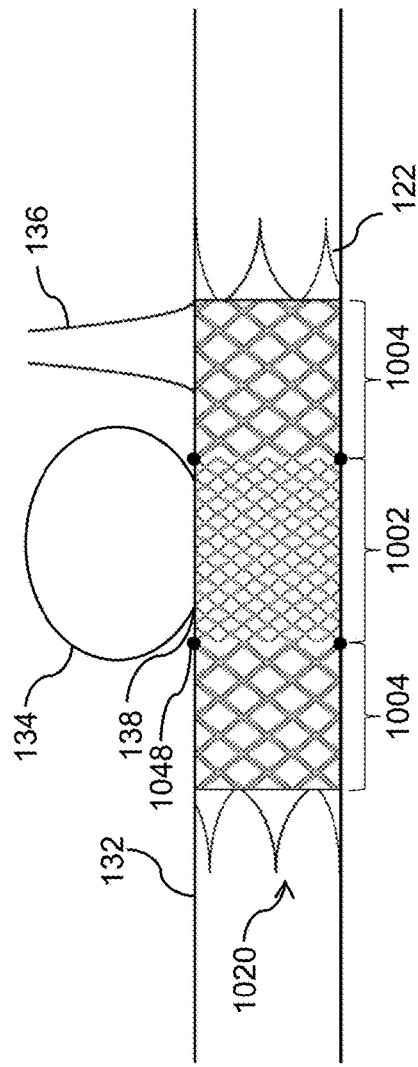

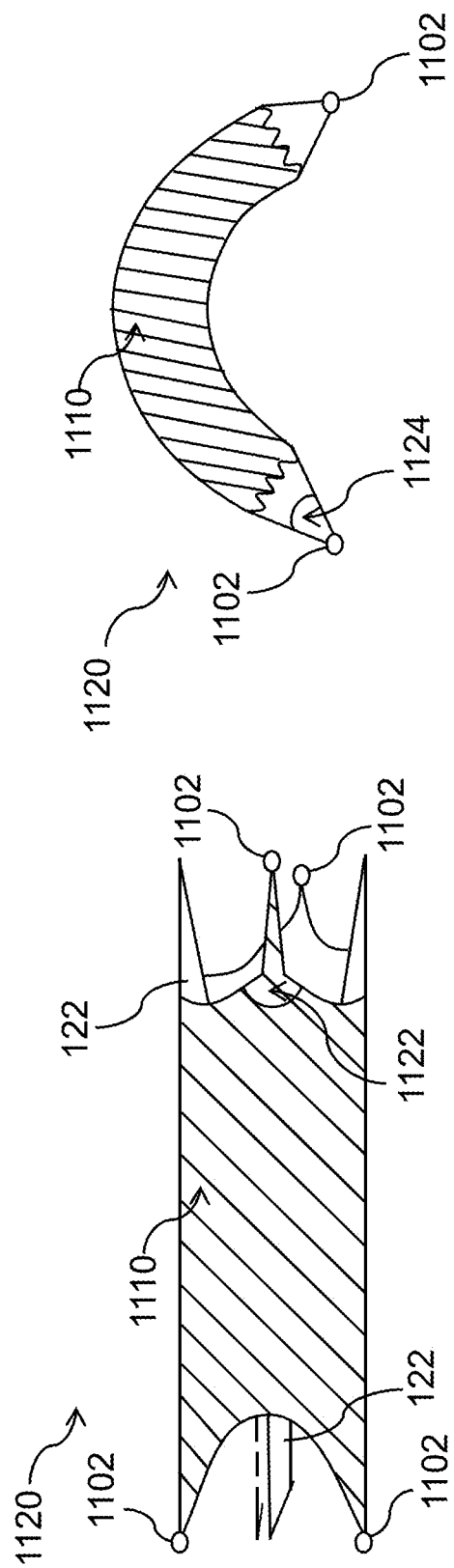

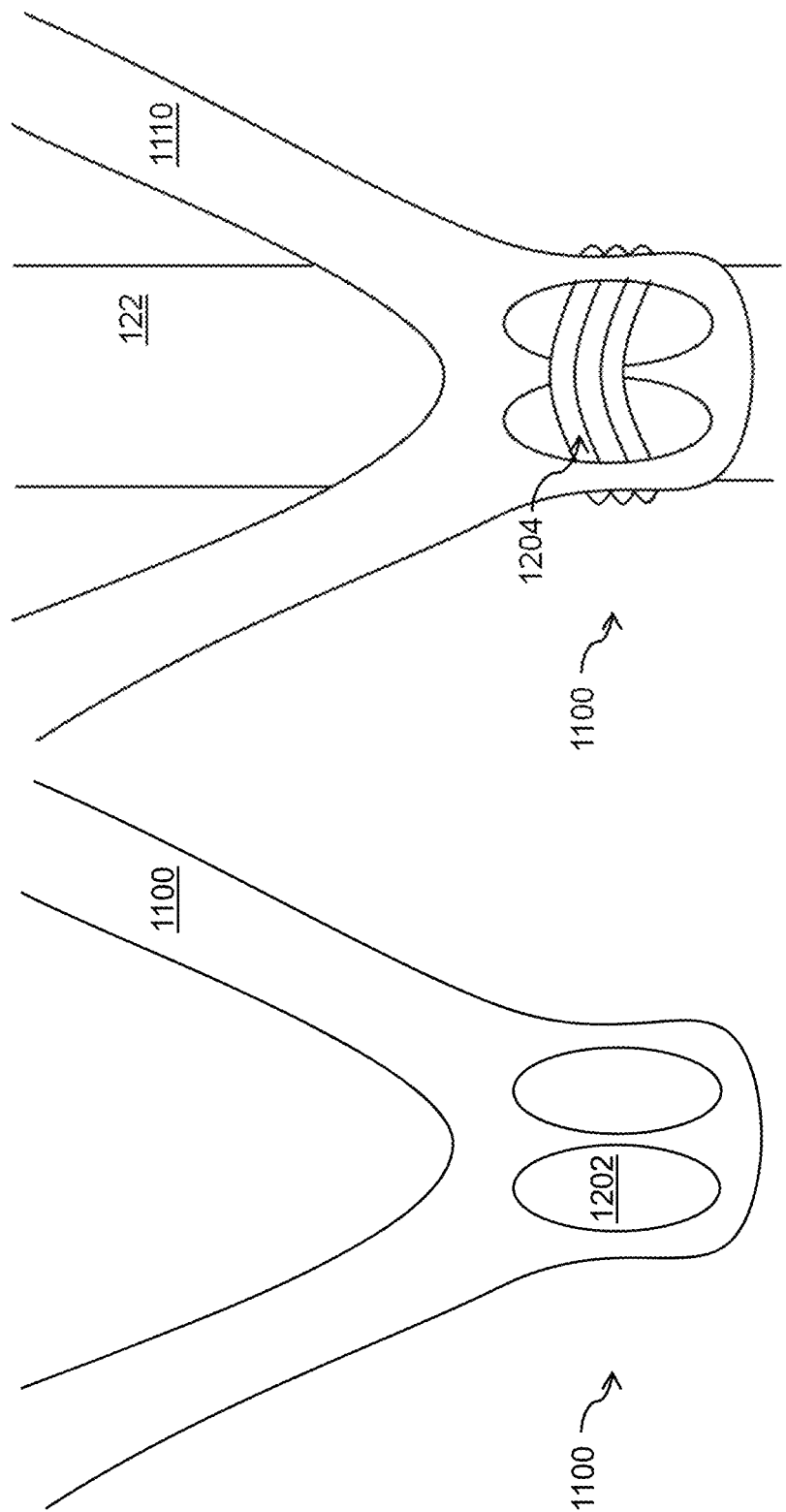

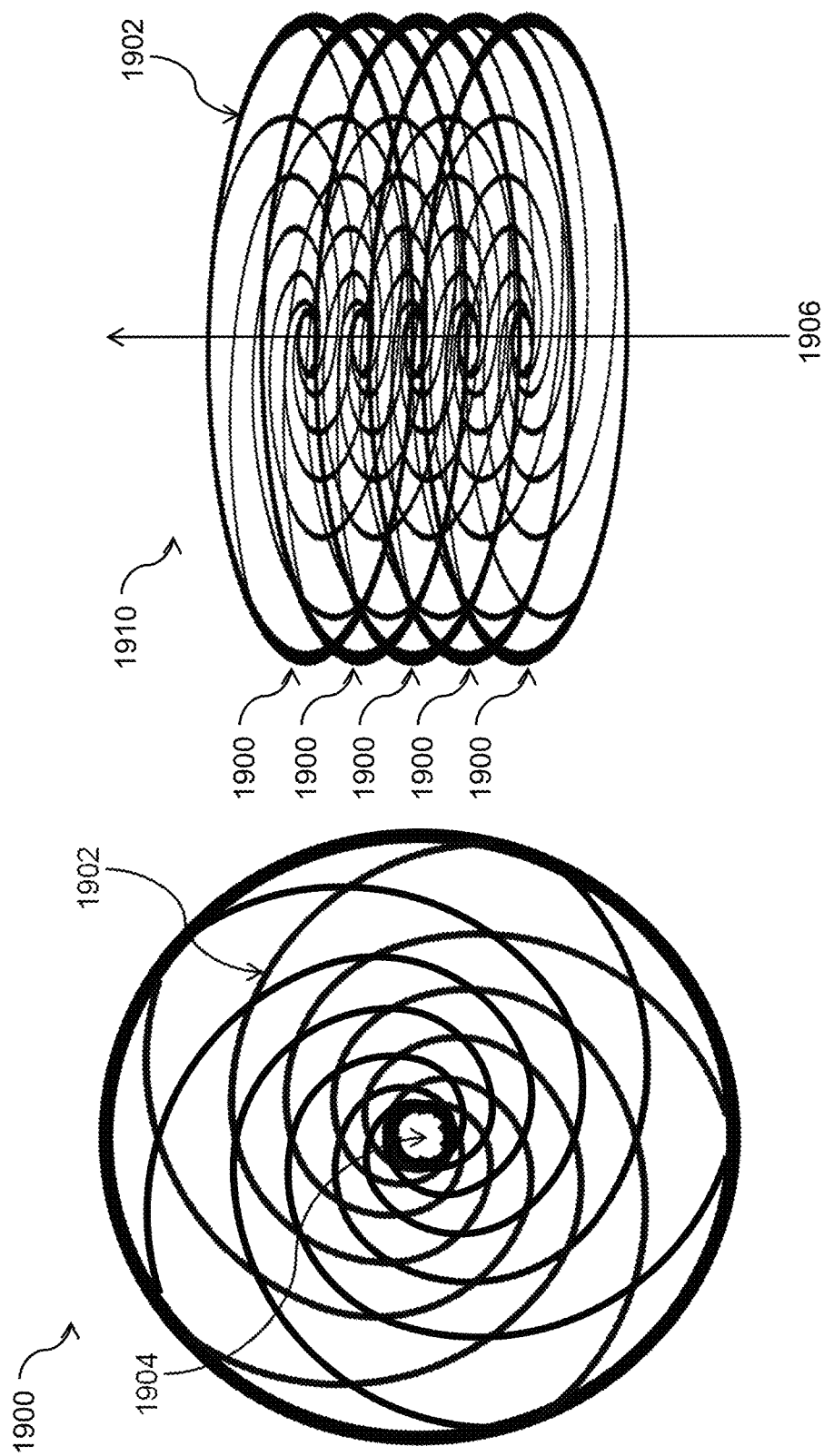

Hexagonal Tiling Patterns

Equilateral Triangular Matrix

THIN-FILM MICROMESH MEDICAL DEVICES AND RELATED METHODS

CROSS-REFERENCES TO RELATED APPLICATIONS

The present application is a continuation of International Application No. PCT/US2016/040864, filed on Jul. 1, 2016, which claims the benefit of U.S. Provisional Application No. 62/188,218, filed on Jul. 2, 2015, U.S. Provisional Application No. 62/209,185, filed on Aug. 24, 2015, U.S. Provisional Application No. 62/209,254, filed on Aug. 24, 2015, and U.S. Provisional Application No. 62/216,965, filed on Sep. 10, 2015, which are hereby incorporated by reference in their entirety.

TECHNICAL FIELD

The present disclosure generally relates to medical devices and, more particularly, to thin-film micromeshes for medical devices and related methods.

BACKGROUND

Aneurysms in blood vessels are relatively common in aging patients. The corresponding blood vessel may rapidly hemorrhage, perhaps mortally, if such aneurysms rupture. Given the extreme health risk, stent devices, such as flow diverter stents, have been developed to treat aneurysms. A conventional stent typically is a braided wire device that is compressed and delivered using a catheter and guide wire to the desired location. The braided wire device diverts blood flow such that the pressure on the aneurysm is significantly reduced, blood flow in the aneurysm sac is diminished so that it occludes, and the aneurysm thereby no longer poses imminent danger of rupture to the patient.

A known complication of conventional stent devices is the phenomenon of delayed aneurysm rupture. This occurs when a patient is seemingly successfully treated with a stent device, but weeks or months later the aneurysm bursts, causing hemorrhagic stroke and death. Accordingly, there is a need in the art for improved stent devices that reduce the rate of delayed aneurysm rupture and achieve higher occlusion rates.

In tissue engineering, cells are often implanted or seeded into scaffolds, such as cell scaffolds, that support growth of a three-dimensional tissue. Conventional scaffolds are typically made using hydrogels, fibrin-based gels, extracellular matrix components, and electrospun polymers. A significant problem in tissue engineering is fabrication and design of scaffolds that facilitate confluent, healthy cellular growth in a controlled manner (e.g., can adopt a desired three-dimensional conformation), facilitate cell to cell interactions so that nutrient and information exchange can occur, and provide mechanical integrity so that they can withstand physiologic stress without fracture or some other form of mechanical compromise.

Conventional scaffolds are either too brittle or too malleable, and suffer from the inability to engineer exact pore configurations given that they rely on a random distribution of pores. Conventional scaffolds thus fail to achieve the desired conformation, strength, and controlled porosity. Accordingly, there is a need in the art for improved scaffolds that can achieve the desired conformation, strength, and controlled porosity.

BRIEF DESCRIPTION OF THE DRAWINGS

FIGS. 2A-B are close-up images of a portion of a thin-film micromesh according to an embodiment.

FIG. 2C is a close-up image of a portion of a thin-film micromesh after exposure to whole blood according to an embodiment.

FIG. 2D is an image of a thin-film micromesh device according to an embodiment.

FIGS. 5A-H are diagrammatic top plan views of layers being formed on a substrate to fabricate a thin-film micromesh according to an embodiment.

FIGS. 6A-B illustrate thin-film micromesh fenestration designs that have the same porosity but different pore densities according to one or more embodiments.

FIGS. 7A-C are diagrammatic top plan views of portions of thin-film micromeshes with different percent metal coverages (PMC) and pore densities according to one or more embodiments.

FIGS. 8A-B illustrate a fenestration of a thin-film micromesh before and after expansion according to an embodiment.

FIG. 10A is a diagrammatic top plan view of a portion of a variable porosity thin-film micromesh according to an embodiment.

FIG. 10B is a diagrammatic top plan view of a portion of a variable porosity thin-film micromesh after expansion according to an embodiment.

FIG. 10C is a diagrammatic side elevational view of a variable porosity thin-film micromesh device with an intermediate higher pore density region flanked by lower pore density regions on both sides according to an embodiment.

FIG. 10D is a diagrammatic side elevational view of a variable porosity thin-film micromesh device with a higher pore density region on one side and a lower pore density on the other side according to an embodiment.

FIG. 10E is a diagrammatic cross-sectional view of a blood vessel with an aneurysm in which a variable porosity thin-film micromesh device is inserted according to an embodiment.

FIG. 11F is a diagrammatic side elevational view of a thin-film mesh device including a thin-film micromesh attached to a backbone at one or more attachment points/areas according to an embodiment.

FIG. 11G is a diagrammatic side elevational view of a thin-film mesh device that is bent in which a thin-film micromesh is held in place by attachment points/areas according to an embodiment.

FIGS. 12A-B are diagrammatic close-up views of an attachment point/area with holes according to an embodiment.

FIG. 19A is a diagrammatic top plan view of a double-spiral thin-film micromesh membrane according to an embodiment.

FIG. 19B is a diagrammatic perspective view of a three-dimensional double-spiral thin-film micromesh structure according to an embodiment.

Figure 1A:
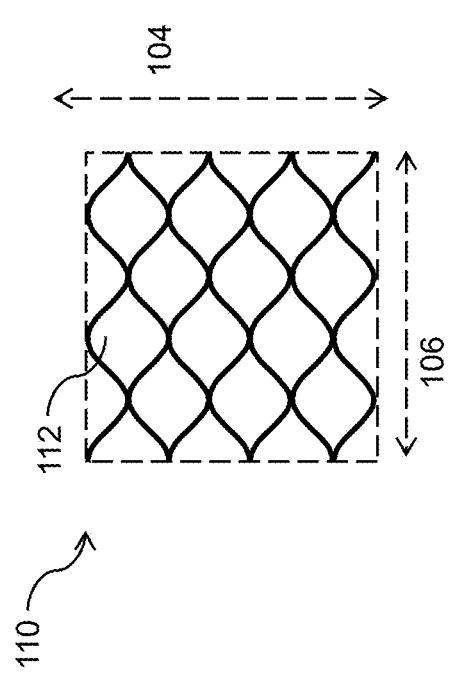
FIG. 1A is a diagrammatic top plan view of a portion of a thin-film micromesh before expansion according to an embodiment.

Embodiments of the present disclosure and their advantages are best understood by referring to the detailed description that follows. It should be appreciated that like reference numerals are used to identify like elements illustrated in one or more of the figures, in which the showings therein are for purposes of illustrating the embodiments and not for purposes of limiting them.

DETAILED DESCRIPTION

Thin-film micromeshes (also referred to as thin-film meshes) for medical devices (e.g., stent devices and scaffold devices) and related methods are provided. As used herein, a thin-film mesh is defined to be less than 100 μm (micrometers or microns) in thickness. In various embodiments, a thin-film mesh is formed using fenestrated thin-film Nitinol (TFN), although other thin-film mesh materials may be used to form the thin-film mesh disclosed herein. The following discussion is thus directed to TFN meshes without loss of generality.

FIGS. 1A-D show a thin-film mesh 100, 110 and a thin-film mesh device 120, a medical device including thin-film mesh 110. FIG. 1A is a diagrammatic top plan view of a portion of thin-film mesh 100 with slits 102 (e.g., closed fenestrations) prior to expansion. Thin-film mesh 100 may be expanded along axis 104, which may be referred to as axis of expansion 104, to open up slits/fenestrations 102 oriented perpendicular to axis 104 and parallel to axis 106, which may be referred to as slit axis 106, by extending thin-film mesh 100 in directions 108 to form thin-film mesh 110 in FIG. 1B and FIG. 1C.

Each of slits/fenestrations 102 may have a slit length of between 25 μm and 500 μm. The slit length may be modulated based on the type of medical device, the type of medical treatment, the body region being treated, and/or the type of aneurysm being treated. For example, the slit length of thin-film mesh 100/110 may be between 50 μm and 300 μm (e.g., between 50 μm and 225 μm, or between 50 μm and 200 μm) to provide thin-film mesh device 120 with advantageous features such as fibrin deposition and cell growth (e.g., endothelialization) when placed in a blood vessel.

The ability of thin-film mesh 100/110 to effectively expand along axis 104 may depend on the length of slits 102. Slits 102 with a longer slit length will result in thin-film mesh 100/110 with increased ability for expansion, while slits 102 with a shorter slit length will result in thin-film mesh 100/110 with a decreased ability for expansion.

Figure 1B:
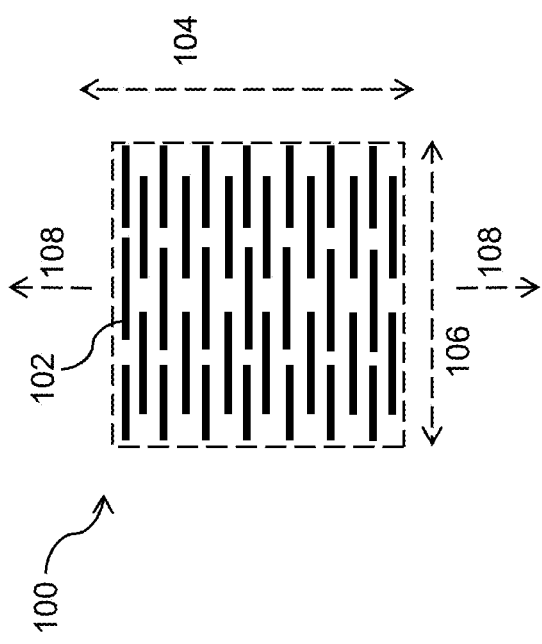
FIG. 1B is a diagrammatic top plan views of a portion of a thin-film micromesh after expansion according to an embodiment.

FIG. 1B is a diagrammatic top plan view of a portion of thin-film mesh 110 including pores 112 (e.g., open fenestrations) after expansion. Thin-film mesh 110 may be formed by expanding thin-film mesh 100 in FIG. 1A. The expansion may extend thin-film mesh 100 along axis 104 such that there is a large increase in length along axis 104 but a small change (e.g., a small decrease) in length along axis 106. In some embodiments, the expansion may extend thin-film mesh 100 along axis 104 in a range from 50% to 800%.

When expanded, slits/fenestrations 102 in FIG. 1A open up into pores/fenestrations 112 to form a "chain-link" fence pattern, such as diamond-shaped pores/fenestrations. Thin-film mesh 110 forms struts around each diamond-shaped pore/fenestration 112. Alternatively, thin-film mesh 110 may be directly formed with diamond-shaped pores 112 (e.g., in its final configuration or partially opened). It will be appreciated that other pore/fenestration shapes may be used in other embodiments.

In one or more embodiments, thin-film mesh 110 has a pore density (fenestrations per square mm) of between 15 pores/mm$^2$ and 2217 pores/mm$^2$, and a percent metal coverage (PMC) of between 6% and 83%. In some embodiments, thin film mesh 110 has a high pore density (e.g., 50 pores/mm$^2$-3000 pores/mm$^2$) and a low metal coverage (e.g., 10%-35%), which may advantageously promote a planar deposition of fibrin followed by rapid cell growth (e.g., endothelialization).

Thin-film mesh 110 may be formed, for example, as a thin-film mesh cover for a stent backbone (e.g., backbone 122 in FIG. 1C and FIG. 2D) or as a thin-film mesh scaffold for tissue engineering (e.g., as described below in relation to FIG. 17). Thin-film mesh 110 may otherwise be included in a medical device for its advantageous properties as further described herein.

Figure 1C:
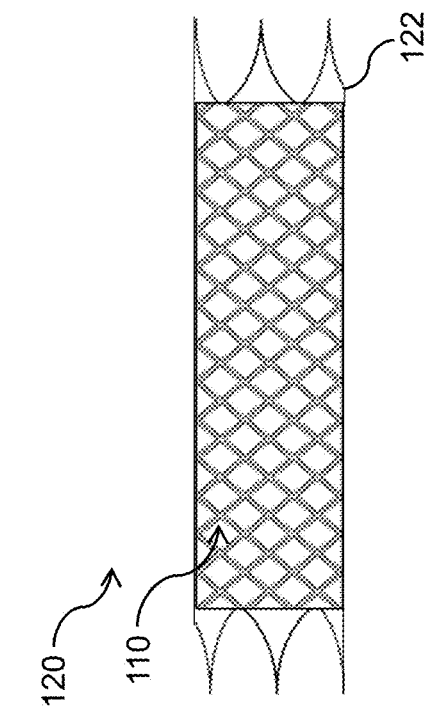
FIG. 1C is a diagrammatic side elevational view of a thin-film micromesh device according to an embodiment.

FIG. 1C is a diagrammatic side elevational view of thin-film mesh device 120 that includes thin-film mesh 110 and a backbone 122 (e.g., a stent backbone). Thin-film mesh 110 expanded to its three-dimensional form (e.g., a cylindrical tube or other shape) may be assembled over backbone 122, which provides structural support for thin-film mesh 110 while maintaining the advantageous features of thin-film mesh 110, such as fibrin deposition and cell growth (e.g., endothelialization) when placed in a blood vessel.

In one or more embodiments, thin-film mesh 100/110 is fabricated as a plurality of layers of thin-film on a substrate such as a silicon wafer using silicon wafer micromachining technology, as described below in relation to FIG. 3, FIGS. 4A-Q, and FIGS. 5A-H. For example, two layers of thin-film may be joined at the two edges either along axis 106 or along axis 104 such that thin-film mesh 100 expands to thin-film mesh 110 formed as a cylindrical tube as shown in FIG. 1C, FIGS. 2D, and 5H. Thin-film mesh 100/110 joined at the two edges along axis 104 and a thin-film covered stent that includes a stent backbone and thin-film mesh 100/110 with axis of expansion 104 oriented parallel to the longitudinal axis of the stent backbone are further described in International Application No. PCT/US2016/39436, filed on Jun. 24, 2016, which claims the benefit of U.S. Provisional Application No. 62/185,513, filed on Jun. 26, 2015, U.S. Provisional Application No. 62/188,218, filed on Jul. 2, 2015, U.S. Provisional Application No. 62/209,185, filed on Aug. 24, 2015, U.S. Provisional Application No. 62/209,254, filed on Aug. 24, 2015, and U.S. Provisional Application No. 62/216,965, filed on Sep. 10, 2015. International Application No. PCT/US2016/39436 and U.S. Provisional Application No. 62/185,513 are hereby incorporated by reference in their entirety.

Figure 1D:
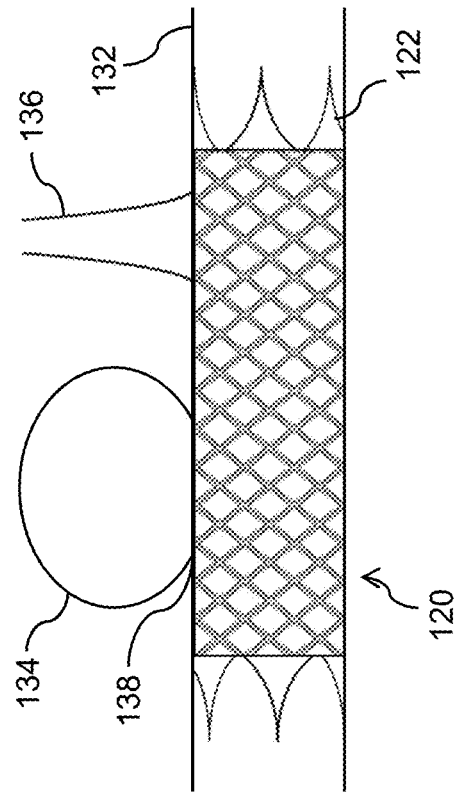
FIG. 1D is a diagrammatic cross-sectional view of a blood vessel with an aneurysm in which a thin-film micromesh device is placed according to an embodiment.

FIG. 1D shows a diagrammatic cross-sectional view of a blood vessel 132 with an aneurysm 134 and a branch vessel 136 (e.g., a branch artery) in which thin-film mesh device 120 of FIG. 1C is implanted. Thin-film mesh device 120 may advantageously be used as a flow diverter due to the properties of thin-film mesh 110. Flow diverters must strike a balance between diverting flow from an aneurysm sac while permitting flow in any perianeurysmal branch vessels. Thin-film mesh 110 advantageously diverts blood flow into aneurysm 134 and promotes rapid deposition of fibrin and endothelialization at a neck 138 of aneurysm 134 so that aneurysm 134 is occluded, while at the same time allowing blood flow through branch vessel 136.

Thin-film mesh device 120 advantageously has a reduced rate of delayed aneurysm rupture when compared to conventional flow diverters. Conventional wire flow diverter stents may provide occlusion of aneurysm necks, but because the pores of such devices are often filled with particles made up of blood coagulation products, inflammatory cells, and cellular debris, such particles may be dislodged and cause delayed aneurysm rupture. Indeed, endothelialization is slow to occur and is often partial at best in conventional wire flow diverter stents. In contrast, thin-film mesh 110 provides a structure on which the blood vessel walls are rapidly rebuilt through endothelialization, promoting a healthy and stable cellular lining, and because the cellular lining is not prone to dislodging as particles of blood coagulation products and the like, the rate of delayed aneurysm rupture is significantly reduced.

FIG. 2A is a close-up image of a portion of an example thin-film mesh 110 that has a pore density of 70 pores/mm$^2$ and a percent metal coverage of 20% before exposure to fibrin. In this example, pores/fenestrations 112 of thin-film mesh 110 has a pore size of 240 µm to 300 µm.

FIG. 2B is a close-up image of a portion of an example thin-film mesh 110 and portions of pores/fenestrations 112. Conventional flow diverter stents made with wire meshes are not flat where the wires intertwine. In contrast, because thin-film mesh 110 is made with a layer of material such as Nitinol and expanded, there is no intertwining of wires. Thus, thin-film mesh 110 is flat all around its pores 112 as shown in FIG. 2B, which is advantageous for promoting rapid deposition of fibrin and cell growth (e.g., endothelialization).

FIG. 2C is a close-up image of a portion of an example thin-film mesh 110 after exposure to fibrin. The fibrin mat facilitates cell growth, and other biomolecules may be incorporated into thin-film mesh 110. In some embodiments, thin-film mesh 110 may advantageously be used as a stent cover for a stent device, as the rapid deposition of fibrin and cell growth (e.g., endothelialization) not only occludes aneurysms but also promotes healing of the blood vessels. In other embodiments, thin-film mesh 110 may advantageously be used as a scaffold (e.g., a membrane or other scaffold structure) for a scaffold device in tissue engineering, as thin-film mesh 110 may be formed having the desired conformation, strength, and controlled porosity. In further embodiments, thin-film mesh 110 may advantageously be included in medical devices that would benefit from planar deposition of fibrin followed by rapid cell growth (e.g., endothelialization) or the ability to be formed with the desired conformation, strength, and controlled porosity.

FIG. 2D shows a side elevational view image of an example thin-film mesh device 120 including backbone 122 and thin-film mesh 110. In some embodiments, thin-film mesh 110 forms a cylindrical tube and may be assembled on backbone 122 by placing thin-film mesh 110 over backbone 122 such that thin-film mesh 110 wraps around backbone 122. Alternatively, thin-film mesh 110 may be attached to the interior surface of backbone 122.

In some embodiments, thin-film mesh 110 includes one or more attachment points or areas that are attached to backbone 122. Radiopaque markers may be used to affix thin-film mesh 110 to stent backbone 122. Examples of attachment points/areas of thin-film mesh 110 and the use of radiopaque markers are further described below in relation to FIGS. 12A-D.

Backbone 122 may be a wire backbone made of metal (e.g., a metal alloy) or a laser-cut backbone fabricated from a metal hypotube. Alternatively, backbone 122 may be a bioabsorbable backbone composed of a bioabsorbable metal or polymeric material that is absorbed, degraded, dissolved, or otherwise fully broken down after a predetermined amount of time (e.g., 3-6 months, 6-24 months, etc.) after implantation in a patient while thin-film mesh 110 remains in the patient. Thin-film mesh device 120 with such bioabsorbable backbone 122 may have advantages compared to medical devices that use a backbone that is not absorbed or does not degrade, which presents potential dangers and risks. For example, long-term presence of a backbone is potentially dangerous because it could serve as a continuing risk for thrombotic complications. Further, the backbone may exert a mechanical force on a parent artery that changes its compliance and flexibility in a manner that may also increase the likelihood of parent artery stenosis. Advantageously, thin-film medical device 120 with bioabsorbable backbone 122 delivers thin-film mesh 110 to a target site (e.g., an aneurysms or arterial disease) while bioabsorbable backbone 122 degrades or is absorbed. For example, bioabsorbable backbone 122 may provide structural support for thin-film mesh 110 while maintaining the advantageous features of thin-film mesh 110, such as fibrin deposition and cell growth (e.g., endothelialization) when placed at the target site such as a blood vessel with an aneurysm. By the time bioabsorbable backbone 122 degrades, the blood vessel may have fully healed and no longer require the mechanical support provided by bioabsorbable backbone 122. In another example, bioabsorbable backbone 122 may simply be a means to deliver thin-film mesh 110 to a target site and not play a major role in aneurysm occlusion and healing of the aneurysm neck region. It will be appreciated that other material or structure may be used for backbone 122 in alternative embodiments.

Figure 3:
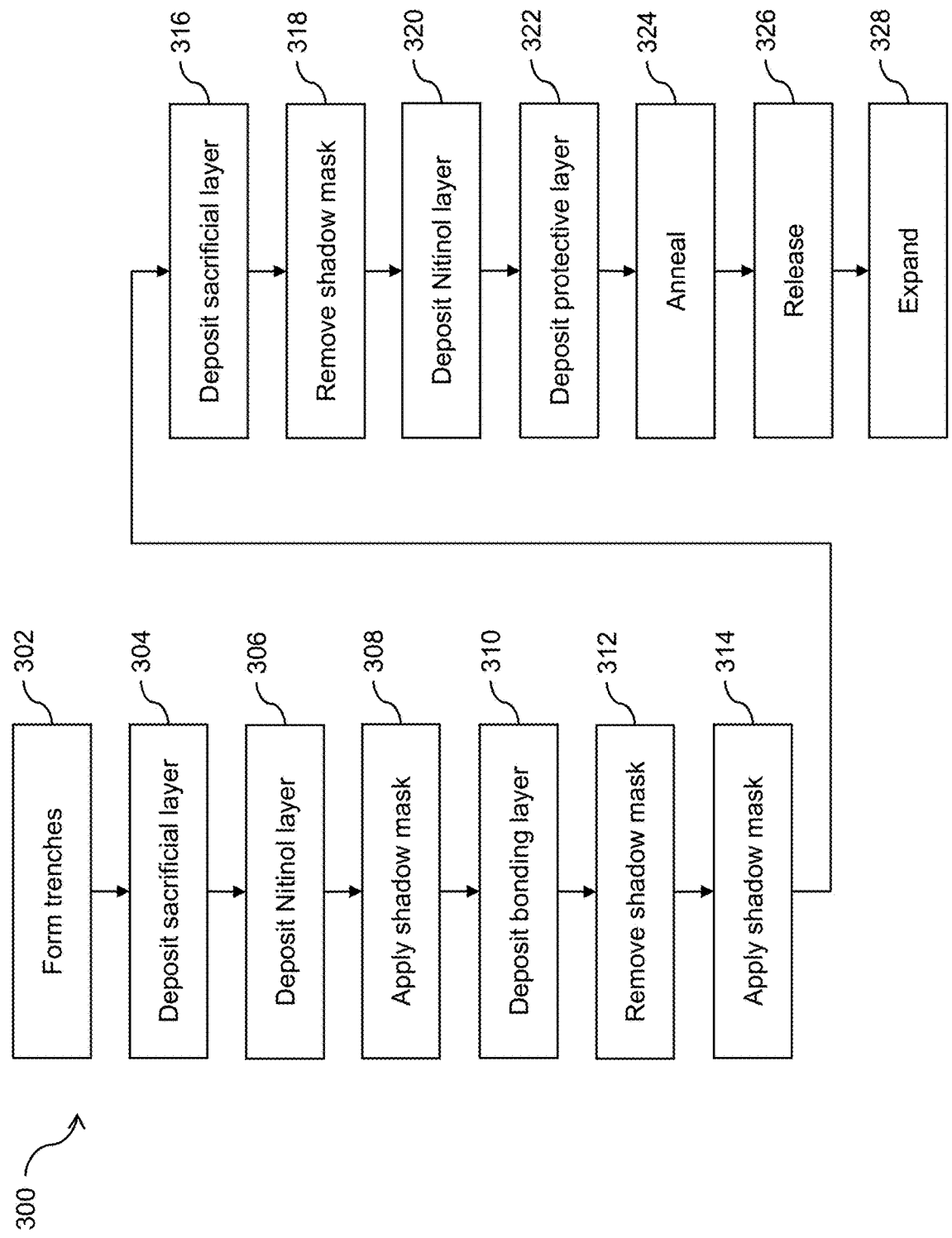
FIG. 3 is a flow diagram of a process to fabricate a thin-film micromesh for a medical device according to an embodiment.
Figures 4A, 4B, 4C, 4D, 4E, 4F, 4G, 4H:
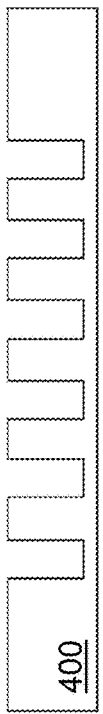
FIGS. 4A-Q are diagrammatic cross-sectional views of layers being formed on a substrate to fabricate a thin-film micromesh according to an embodiment.

FIG. 3 is a flow diagram of a process 300 to fabricate a thin-film mesh, such as thin-film mesh 100/110 of FIGS. 1A-D or FIGS. 2A-D, for a thin-film mesh device, such as thin-film mesh device 120 of FIGS. 1C-D and FIG. 2D. At block 302, trenches are formed on a wafer 400 (e.g., a silicon wafer or other wafer) as shown in FIGS. 4A-4E and 5A-5C. FIGS. 4A and 5A show wafer 400, which may have an oxide layer with a thickness of between 500 nm and 1 μm on top. A photoresist 402 is spun-coated on wafer 400 as shown in FIG. 4B. By patterning and developing photoresist 402 using photolithography, a pattern of exposed areas 404 is formed as shown in FIG. 4C and FIG. 5B. The pattern of exposed areas 404 is available for etching. Deep reactive ion etching (DRIE) is performed to form grooves or trenches 406 that are at least 15 μm deep (e.g., between 25 μm and 200 μm deep) as shown in FIG. 4D, Photoresist 402 is removed and wafer 400 is cleaned, resulting in etched wafer 400 with trenches 406 as shown in FIG. 4E and FIG. 5C. Trenches 406 may form a micropattern that provides a template for thin-film mesh 100. The resolution of the micropattern using the DRIE process may be, for example, approximately 1 μm. Although two micropatterns 502 for two thin-film meshes are shown in FIG. 5C, wafer 400 may include more micropatterns. The term "approximately," as used herein when referring to a measurable value, encompasses variations of ±20%, ±10%, ±5%, ±1%, ±0.5%, or ±0.1% of the value.

At block 304, a sacrificial layer 408 (e.g., a chrome sacrificial layer or a copper sacrificial layer), also referred to as a lift-off layer, is deposited as shown in FIG. 4F. Sacrificial layer 408 may be deposited by sputter deposition or evaporation deposition such as electron beam physical vapor deposition (EBPVD). Sacrificial layer 408 may have a thickness of, for example, 1 μm or less (e.g., approximately 500 nm).

At block 306, a Nitinol layer 410 is deposited as shown in FIG. 4G and FIG. 5D. Nitinol layer 410 may have a thickness of, for example, between 1 μm and 20 μm (e.g., approximately 5 μm). As sputtered Nitinol at regions corresponding to trenches 406 fall to the bottom of trenches 406, the micropattern of trenches 406 of wafer 400 are duplicated on Nitinol layer 410 as corresponding fenestrations (e.g., closed fenestrations) such as slits 102 of thin-film mesh 100 as shown in FIG. 1A. The resulting pattern of fenestrations 102 may also be denoted as a fiche in that fenestrations 102 are in closed form prior to an expansion of thin-film mesh 100. Just like a microfiche, each fiche or pattern of fenestrations 102 effectively codes for resulting fenestrations 112 when thin-film mesh 100 is expanded to fully open up fenestrations 102.

At block 308, a shadow mask 412 is applied as shown in FIG. 4H. Shadow mask 412 is applied to a mesh region 414 and exposes seam regions 416 for deposition of a bonding layer 418.

Figure 4I:
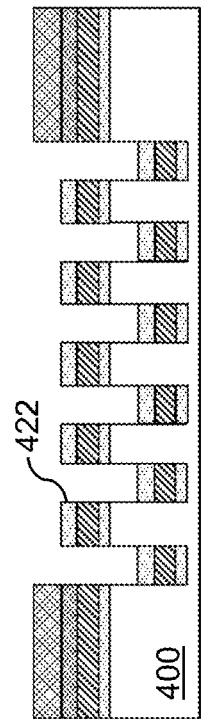

At block 310, bonding layer 418 (e.g., an aluminum bonding layer) is deposited as shown in FIG. 4I. Bonding layer 418 may have a thickness of, for example, 1 μm or less (e.g., approximately 500 nm).

Figure 4J:
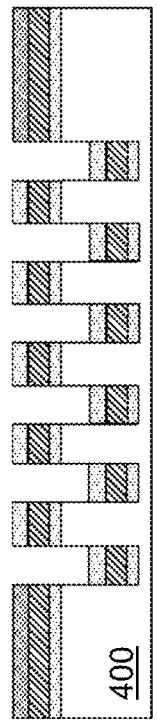

At block 312, shadow mask 412 is removed as shown in FIG. 4J.

Figure 4K:
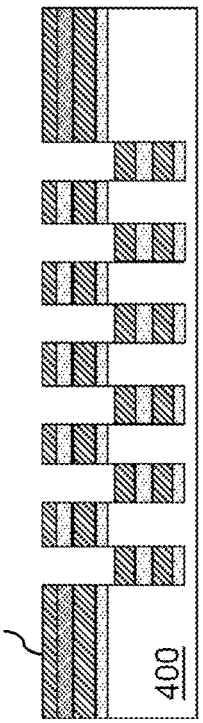

At block 314, a shadow mask 420 is applied as shown in FIG. 4K. Shadow mask 420 is applied to seam regions 416 and exposes mesh region 414 for deposition of a sacrificial layer 422.

Figure 4L:
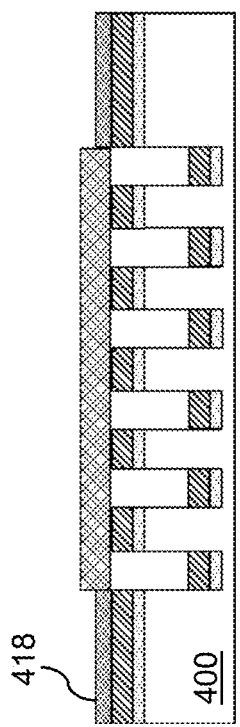

At block 316, sacrificial layer 422 (e.g., a chrome sacrificial layer or a copper sacrificial layer) is deposited as shown in FIG. 4L and FIG. 5E. Sacrificial layer 422 may have a thickness of, for example, 1 μm or less (e.g., approximately 500 nm).

Figure 4M:
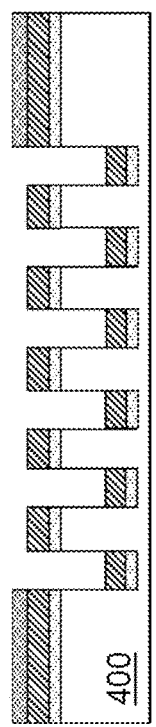

At block 318, shadow mask 420 is removed as shown in FIG. 4M.

Figure 4N:
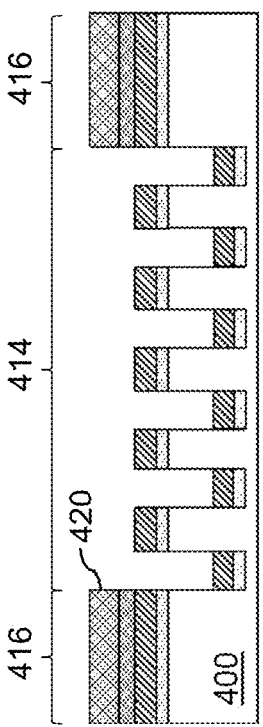

At block 320, a Nitinol layer 424 is deposited as shown in FIG. 4N and FIG. 5F. Nitinol layer 424 may have a thickness of, for example, between 1 μm and 50 μm (e.g., approximately 5 μm). Similarly to block 306, as sputtered Nitinol at regions corresponding to trenches 406 fall to the bottom of trenches 406, the micropattern of trenches 406 of wafer 400 are duplicated on Nitinol layer 424 as corresponding fenestrations (e.g., closed fenestrations) such as slits 102 of thin-film mesh 100 as shown in FIG. 1A.

Figure 4O:
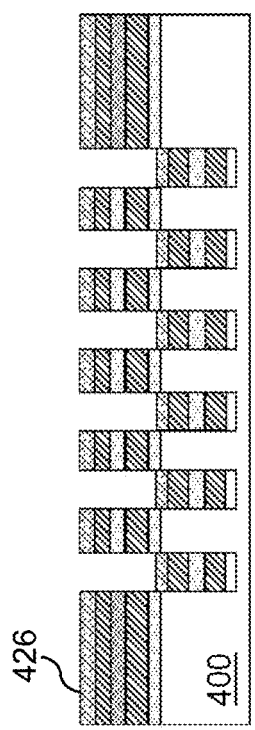

At block 322, a protective layer 426 (e.g., a protective chrome layer) is deposited as shown in FIG. 4O. Protective layer 426 may have a thickness of, for example, 1 μm or less (e.g., approximately 500 nm).

Figure 4P:
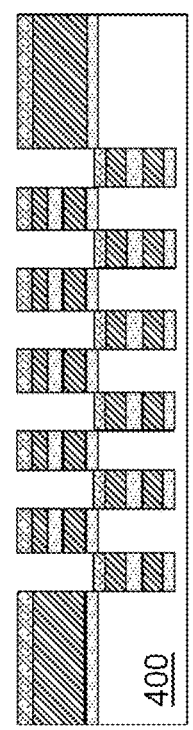

At block 324, Nitinol layers 410, 424 and bonding layer 418 are annealed to form thin-film mesh 100 as shown in FIG. 4P. Wafer 400 with Nitinol layers 410, 424 and bonding layer 414 may be annealed at a high temperature (e.g., approximately 675° C. for approximately 10 minutes) to melt bonding layer 418 and crystalize amorphous Nitinol layers 410, 424. Nitinol layer 410 and Nitinol layer 424 are fused in inseam region 416.

Figure 4Q:

At block 326, thin-film mesh 100 is released as shown in FIG. 4Q and FIG. 5G. Annealed wafer 400 may be placed in chrome etchant (e.g., for approximately 1 hour) to release thin-film mesh 100 from top of the wafer 400.

At block 328, thin-film mesh 100 is expanded to form a three-dimensional thin-film mesh 110 with fenestrations 112 that have been opened up such as a cylindrical tube as shown in FIG. 5H. It will be appreciated that combining the lift-off process with multiple-layer depositions of Nitinol separated by layers of sacrificial layers enables fabrication of thin-film meshes 110 of various other three-dimensional shapes in other embodiments. Further descriptions and examples of fenestrated TFN and three-dimensional fabrication techniques are disclosed in International Application No. PCT/US2014/61836, filed Oct. 22, 2014, which claims the benefit of U.S. Provisional Application No. 61/894,826, filed Oct. 28, 2013, and U.S. Provisional Application No. 61/148,689, filed Apr. 17, 2015, which are hereby incorporated by reference in their entirety.

FIGS. 6A-B illustrate thin-film mesh fenestration designs that have the same porosity but different pore densities. The primary characteristics that determine the degree of flow diversion are percent metal coverage (PMC) and pore density, where higher percent metal coverage and higher pore density yield an increased flow diverting effect. Percent metal coverage is the fraction of the area of metal over the total area. Porosity is the fraction of the open area over the total area. Accordingly, for expanded thin-film mesh 110, the porosity (in percentage) and percent metal coverage of thin-film mesh 110 add up to 100%. Similarly, for thin-film mesh device 120, the porosity of thin-film mesh device 120 (in percentage), the percent metal coverage of thin-film mesh 110, and the percent metal coverage of backbone 122 add up to 100%.

The surface shown in FIG. 6A has a length 602 of 1 mm and a pore length 604 of 0.71 mm, such that the surface has a porosity of 50%, a pore density of 1 pore/mm$^2$, and a total edge length of 2.84 mm. The surface shown in FIG. 6B has a length 602 of 1 mm and a pore length 606 of 0.24 mm, such that the surface has a porosity of 50%, a pore density of 9 pore/mm$^2$, and a total edge length of 8.64 mm. Even though the pore designs of FIG. 6A and FIG. 6B have the same porosity of 50%, the design in FIG. 6A has a pore density of 1 pore/area while the design in FIG. 6B has a pore density of 9 pores/area. For flow diverter stents, two flow diverter stents having similar porosity and percent metal coverage may have drastically different efficacy due to different pore density. For example, thin-film mesh device 120 with a percent metal coverage of 10-15% and 50-100 pores/mm$^2$ are more effective compared to a conventional flow diverter stent having a percent metal coverage of 35% and 14 pores/mm$^2$. Thin-film mesh device 120 with a percent metal coverage of 25-35% and 150-250 pores/mm$^2$ are even more effective compared to conventional flow diverter stents having a percent metal coverage of 35% and 14 pores/mm$^2$ because the increased pore density provides more friction per unit area and provides a surface for fibrin deposition and cell growth (e.g., endothelialization).

FIGS. 7A-C are diagrammatic top plan views of portions of thin-film meshes 110 with different percent metal coverages (PMC) and pore densities. As shown in FIG. 7A, thin-film mesh 110 has a percent metal coverage of 12.8%, a pore density of 70 pores/mm$^2$, and a pore size of 300 μm. As shown in FIG. 7B, thin-film mesh 110 has a percent metal coverage of 15.3%, 100 pores/mm$^2$, and a pore size of 225 As shown in FIG. 7C, thin-film mesh 110 has a percent metal coverage of 25.2%, 175 pores/mm$^2$, and a pore size of 100 μm. In some embodiments, thin-film mesh 110 may have a percent metal coverage of between 17% and 66% and a pore density of between 16 pores/mm$^2$ and 1075 pores/mm$^2$. In other embodiments, thin-film mesh 110 may have a percent metal coverage of 19-47% and a pore density of 81 pores/mm$^2$ and 424 pores/mm$^2$. It will be appreciated that other percent metal coverage and pore density amounts may be used in further embodiments.

FIGS. 8A-B illustrate fenestration 112 of thin-film mesh 100 before and after expansion. FIG. 8A illustrates slit 102 (e.g., a closed fenestration) and a surrounding struts 116 of thin-film mesh 110 before expansion. Surrounding struts 116 may have a strut width 802, which may be between 1 and 25 μm. Slit 102 may have a slit width 804 and a slit length 114. One half of slit width may be referred to as $Y_1$, and one half of slit length 114 may be referred to as $X_1$.

FIG. 8B illustrates pore 112 (e.g., an open fenestration) and surrounding strut 116 of thin-film mesh 110 after expansion. Surrounding strut 116 may have a strut width 802, which may be between 1 and 25 μm. Diamond-shaped pore 112 may have a short diagonal length 814 along short diagonal axis such as axis 104 of FIGS. 1A-B, a long diagonal length 816 along long diagonal axis such as axis 106 of FIGS. 1A-B, and a side length 820. Diamond-shaped pore 112 may further have a strut angle θ 818. In some embodiments, strut angle θ 818 may be between 30 and 90 degrees. Length 824, which is one half of short diagonal length 814, may be referred to as $Y_2$, and length 826, which is one half of long diagonal axis 816, may be referred to as $X_2$.

As side length 820 is equal or approximately equal to half of slit length 114 in FIG. 8A (given that pore 112 open up from slit 102), side length 820 may equal or be approximated as $X_1$. The lengths $X_1$, $X_2$, and $Y_2$, and strut angle θ may be related by the following equations:

$$\cos\frac{\theta}{2} = \frac{X_2}{X_1}$$

$$\sin\frac{\theta}{2} = \frac{Y_2}{X_1}$$

Accordingly, a percentage change in X (along axis 106) and a percentage change in Y (along axis 104) may be calculated. For example, if slit length 114 is 150 μm and slit width 804 is 10 μm, and strut angle θ 818 is 45°, then: $X_1$=75 μm, $Y_1$=5 μm, $X_2$=69.3 μm, and $Y_2$=28.7 μm. The percent change in X is small, −7.6%, when compared to the percent change in Y, 474%.

Further, other features of diamond-shaped pores 112 may be determined by the following equations:

$$\text{Pore area} = 2X_2Y_2$$

$$\text{Pore area with strut metal} = 2(X_2+W)(Y_2+W)$$

$$\text{Pore density} = \frac{1}{2(X_2+W)(Y_2+W)}$$

$$\text{Percent metal coverage} = 1 - \frac{2X_2Y_2}{2(X_2+W)(Y_2+W)}.$$

For example, if slit length 114 is 150 μm, slit width 804 is 10 μm, strut width 802 is 8 μm, and strut angle θ 818 is 30°, then: $X_1$=75 μm, $Y_1$=5 μm, $X_2$=72 μm, $Y_2$=19 μm, pore area=0.0027 mm$^2$, pore area with strut metal=0.0043 mm$^2$, pore density=230 pores/mm$^2$, and percent metal coverage=37%.

Figure 9A:
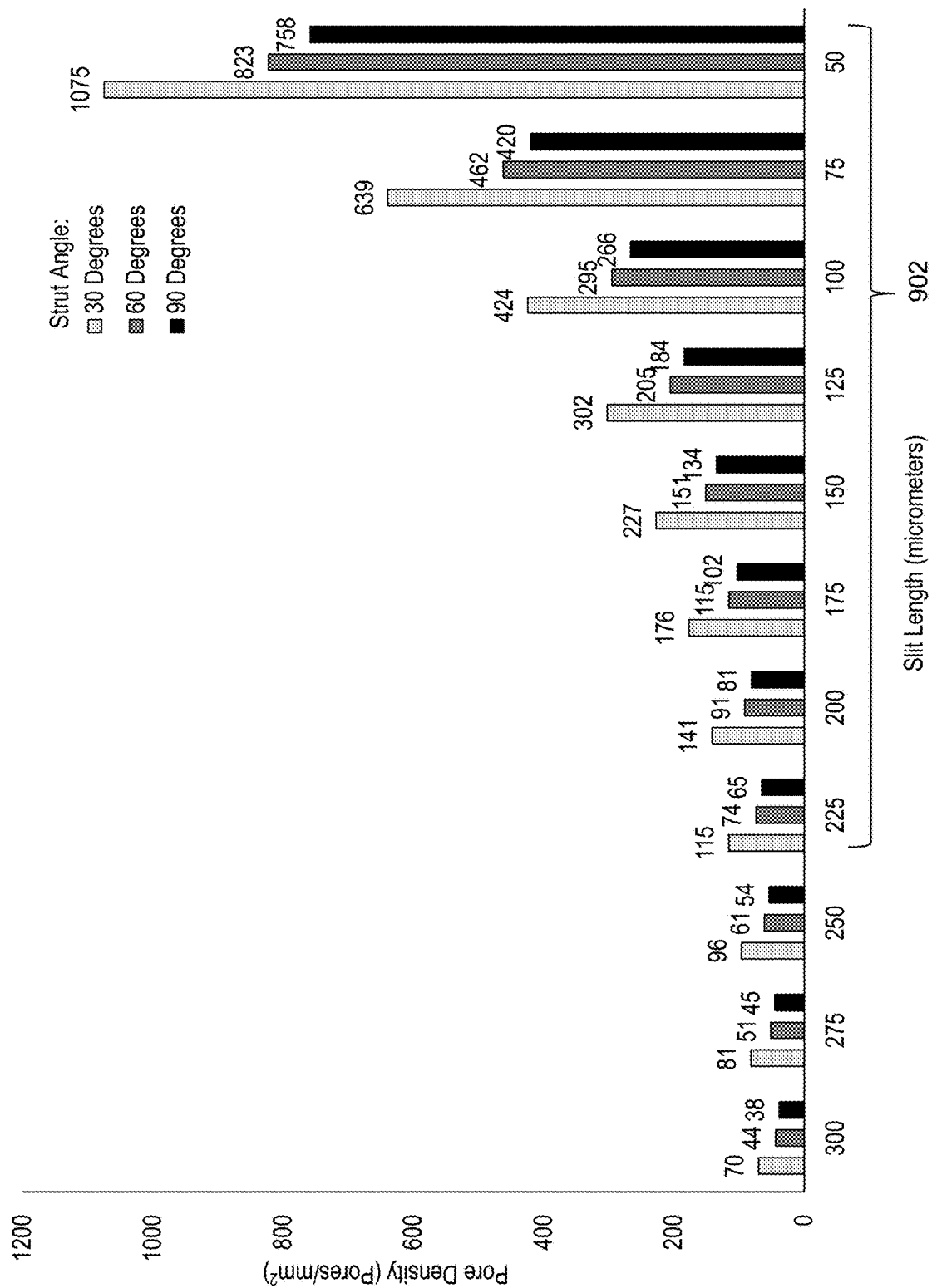
FIGS. 9A-C are graphs characterizing thin-film micromeshes according to one or more embodiments.
Figure 9B:
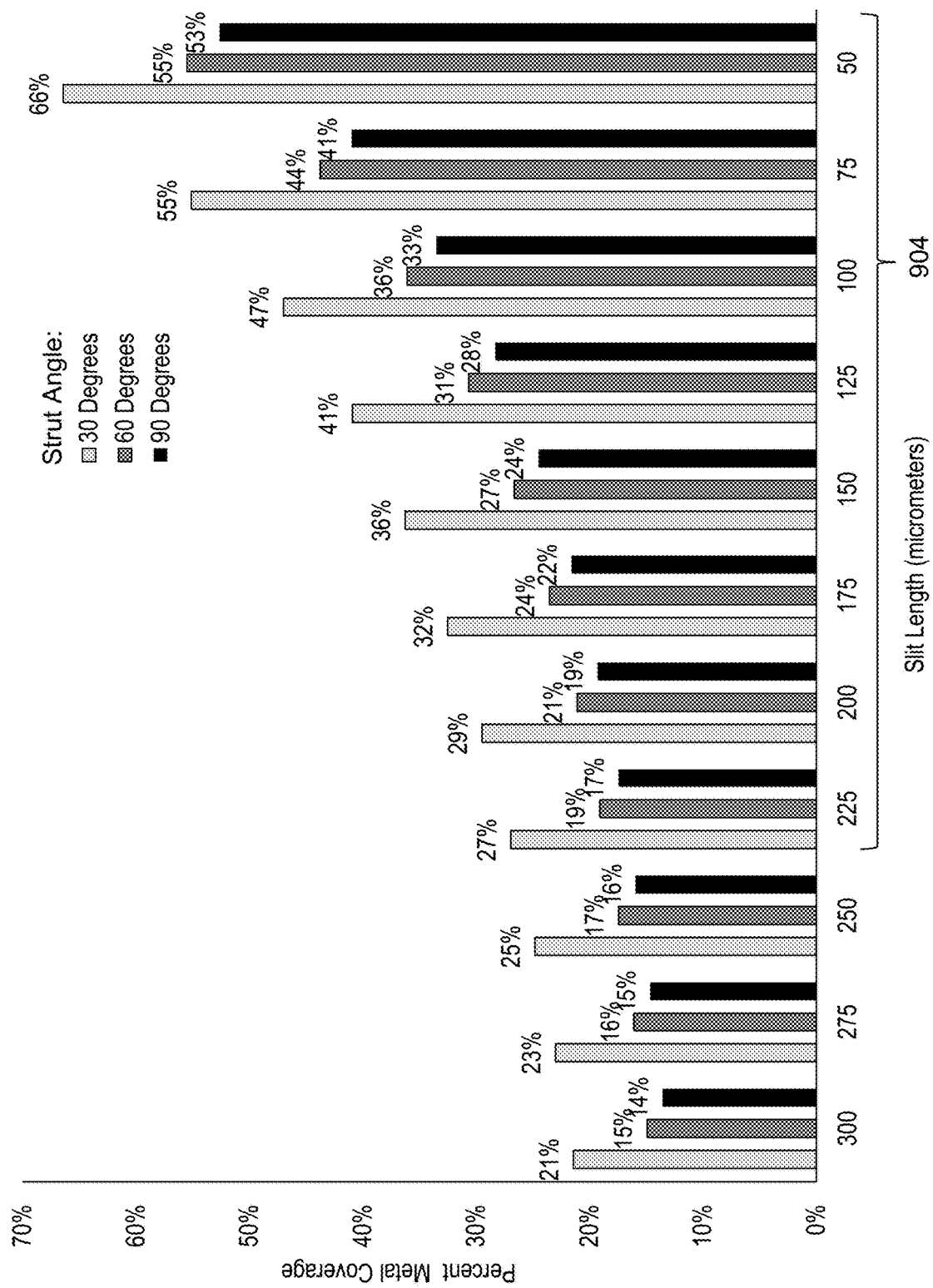
Figure 9C:
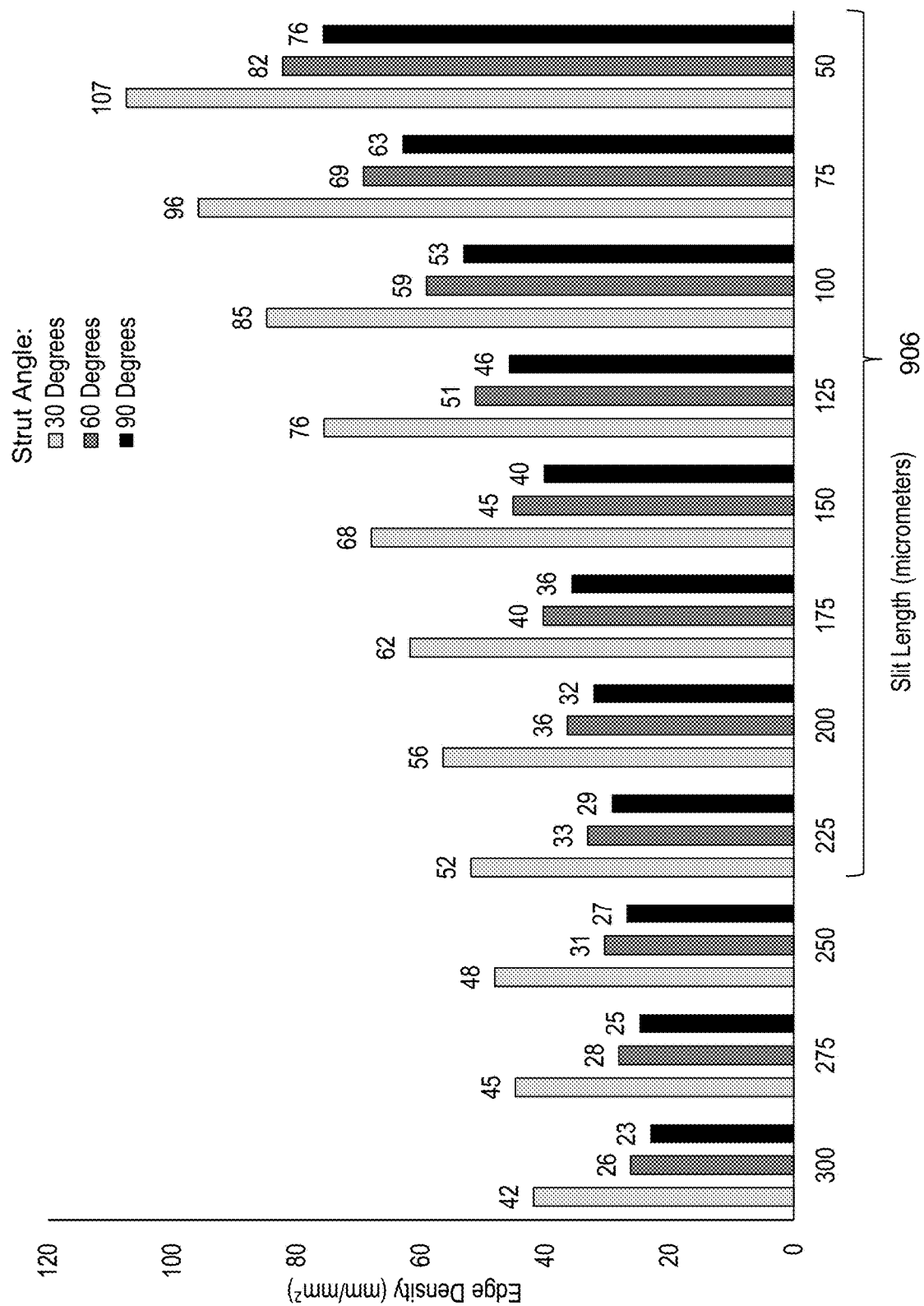

FIGS. 9A-C are graphs characterizing thin-film meshes 110. FIG. 9A shows a graph of pore density vs. slit length 114, assuming an 8 μm strut width. FIG. 9B shows a graph of percent metal coverage vs. slit length 114, assuming an 8 μm strut width. FIG. 9C shows a graph of edge density vs. slit length 114, assuming an 8 μm strut width. The ranges of physical characteristics—slit length 114, pore density, percent metal coverage, and edge density—with advantageous properties including rapid fibrin deposition and cell growth (e.g., endothelialization) are shown as 902, 904, and 906 in FIGS. 9A-C.

In some embodiments, thin-film mesh 110 has a slit length shown in FIGS. 9A-C, where any value may form an upper end point or a lower end point, as appropriate. Thin-film mesh 110 may have a pore density shown in FIG. 9A, where any value may form an upper end point or a lower end point, as appropriate. Thin-film mesh 110 may also have a percent metal coverage shown in FIG. 9B, where any value may form an upper end point or a lower end point, as appropriate. Further, thin-film mesh 110 may have an edge density shown in FIG. 9C, where any value may form an upper end point or a lower end point, as appropriate.

In an example, thin-film mesh 110 has a slit length between 50 μm and 225 μm. Thin-film mesh has a pore density corresponding to a slit length of between 50 μm and 225 μm shown in FIG. 9A (as indicated by 902). Thin-film mesh 110 also has a percent metal coverage corresponding to a slit length of between 50 μm and 225 μm shown in FIG. 9B (as indicated by 904). Thin-film mesh 110 has an edge density corresponding to a slit length of between 50 μm and 225 μm shown in FIG. 9C (as indicated by 906).

In another example, thin-film mesh 110 has a slit length between 100 μm and 150 μm. Thin-film mesh has a pore density corresponding to a slit length of between 100 μm and 150 μm shown in FIG. 9A. Thin-film mesh 110 also has a percent metal coverage corresponding to a slit length of between 100 μm and 150 μm shown in FIG. 9B. Thin-film mesh 110 has an edge density corresponding to a slit length of between 100 μm and 150 μm shown in FIG. 9C.

FIGS. 10A-E show a variable porosity thin-film mesh 1000, 1010 and a variable porosity thin-film mesh device 1020. FIG. 10A is a diagrammatic top plan view of a portion of variable porosity thin-film mesh 1000 with slits 1012, 1014 (e.g., closed fenestrations) prior to expansion. Variable porosity thin-film mesh 1000 includes at least one region 1002 with a density of slits 1012 that is higher than a density of slits 1014 in at least one other region 1004. Slits 1012 in region 1002 may be smaller than slits 1014 in region 1004.

When thin-film mesh 1000 is fabricated, Nitinol layers 410 and 424 in FIGS. 4G and 4N may be deposited in a shape that is wider in higher pore density region 1002 than low pore density region 1004 to account for less expansion in higher pore density region 1002. For example, thin-film mesh 1000 may be wider in middle region 1002 where pore density is higher than side regions 1004 where pore density is lower.

FIG. 10B is a diagrammatic top plan view of a portion of variable porosity thin-film mesh 1010 including pores 1016, 1018 (e.g., open fenestrations) after expansion. Variable thin-film mesh 1000 in FIG. 10A may be expanded in directions 1006 such that slits/fenestrations 1012 and 1014 open up to pores 1016 and 1018 to form a "chain-link" fence pattern with a variable pore density and percent metal coverage along an axis 1008, which may be referred to as axis of variable porosity 1008. In some embodiments, the expansion may extend thin-film mesh 1000 in a range from 50% to 800%. It will be appreciated that other pore/fenestration shapes may be used in alternative embodiments.

Variable porosity thin-film mesh 1010 may include at least one region 1002 with a density of pores 1016 that is higher than a density of pores 1018 in at least one other region 1004. The pore density of thin-film mesh 1010 may vary along axis of variable porosity 1008. Pores 1016 in high pore density region 1002 may be smaller than pores 1018 in low pore density region 1004.

FIGS. 10C and 10D are diagrammatic side elevational views of thin-film mesh devices 1020 that include thin-film meshes 1010 assembled on backbones 122. Thin-film mesh 1010 may have a pore density that varies along the longitudinal length of backbone 112, and axis 1008 may further be referred to as long/longitudinal axis 1008 of backbone 112. In some embodiments, thin-film mesh device 1020 includes high pore density region 1002 and low pore density regions 1004 flanking both sides of region 1002 as shown in FIG. 10C, In other embodiments, thin-film mesh device 1020 includes region 1002 on one side and region 1004 on the other side of thin-film mesh device 1020 as shown in FIG. 10D.

FIG. 10E is a diagrammatic cross-sectional view of blood vessel 132 with aneurysm 134 and branch vessel 136 in which thin-film mesh device 1020 of FIG. 10C is inserted. Thin-film mesh device 1020 may be placed such that high pore density region 1002 is at aneurysm neck region 138, and low pore density region 1004 is at or near branch vessels 136. Advantageously, a higher pore density and higher percent metal coverage may be achieved at aneurysm neck 138 by placing high pore density region 1002 at aneurysm neck 138, thereby reducing blood flow from flowing into the aneurysm, such as intra-aneurysmal flow, and promote faster healing and more robust scaffold for parent artery reconstruction and endothelialization. Further, a low pore density and low percent metal coverage may be achieved at nearby branch vessels 136 by placing low pore density region 1004 at regions other than aneurysm neck 138, thereby facilitating vessel healing while allowing better blood flow through branch arteries and, thus, making the device safer for patients. In some embodiments, thin-film mesh device 1020 may include one or more radiopaque markers 1048 that delineate the transition zone between region 1002 and region 1004. In other embodiments, the variation in pore density may be gradual such that there is no transition zone, in which case radiopaque markers 1048 (e.g., gold markers) may be positioned relative to an area having a higher pore density. In further embodiments, thin-film mesh 1010 may only include high pore density region 1002 that is placed over a defined portion of stent 122 (e.g., in the middle or on one side) and forego low pore density region 1004 altogether.

Figure 11B:
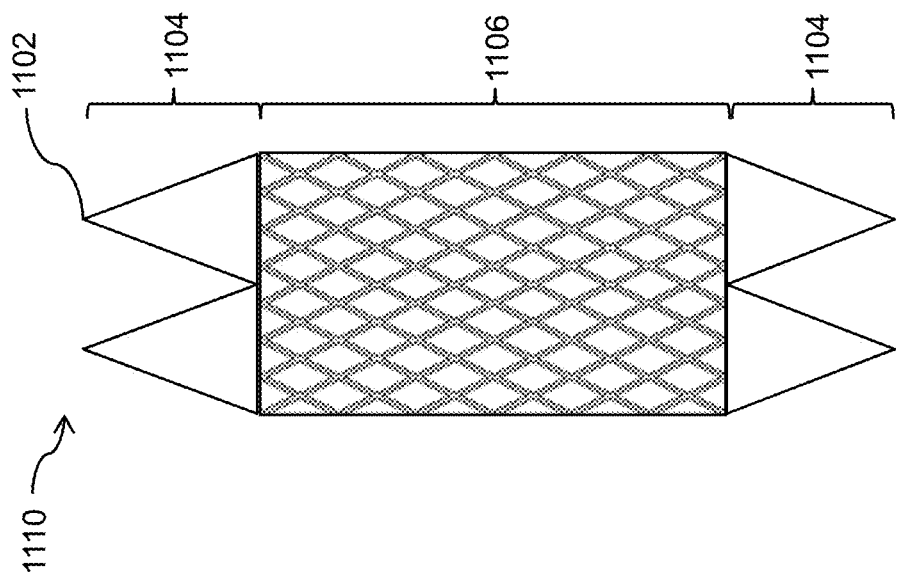
FIG. 11B is a diagrammatic top plan view of a thin-film micromesh with one or more attachment points/areas after expansion according to an embodiment.
Figure 11A:
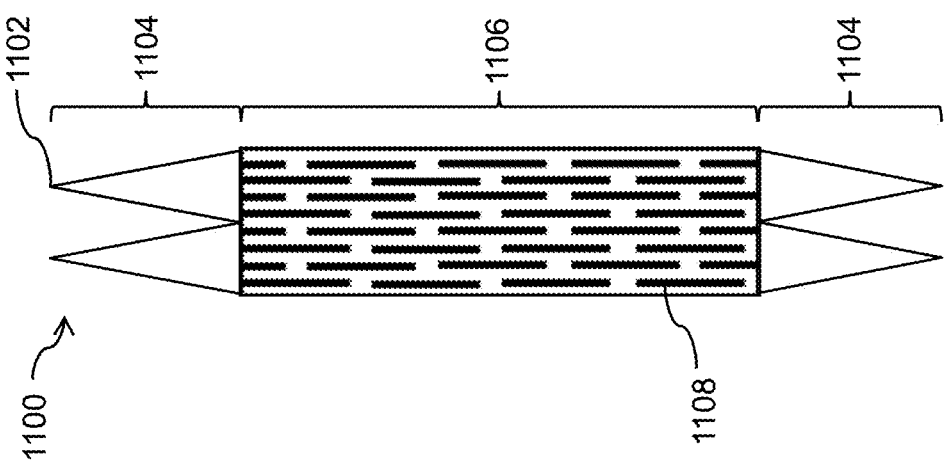
FIG. 11A is a diagrammatic top plan view of a thin-film micromesh with one or more attachment points or areas before expansion according to an embodiment.

FIGS. 11A-G show thin-film meshes 1100, 1110 and thin-film mesh devices 1120 including one or more attachment points/areas 1102. FIG. 11A is a diagrammatic top plan view of thin-film mesh 1100 prior to expansion that includes one or more attachment points/areas 1102 at the end of narrowing regions 1104 (e.g., having triangular shapes) and a region 1106 with pores/fenestrations 1108. Thin-film mesh 1100 may have a width of, for example, between approximately 25 μm and 50 μm prior to expansion. Fenestrations 1108 may be provided at narrowing regions 1104 (not shown) with the same pore density as region 1106 or a varying/graduated pore density. Each of attachment points/areas 1102 are configured to be attached to a backbone or a scaffold such as backbone 122 in FIGS. 1C-D and 2D. Examples of attachment points/areas 1102 are shown in FIGS. 12A-B and 13A-B.

FIG. 11B is a diagrammatic top plan view of thin-film mesh 1110 after expansion. Thin-film mesh 1110 may be formed by expanding thin-film mesh 1100. Thin-film mesh 1110 may have a width of, for example, between approximately 50 μm and 400 μm after expansion. The angle at attachment point/area 1102 of thin-film mesh 1110 after expansion may be larger than the angle at attachment point/area 1102 of thin-film mesh 1100 prior to expansion.

Figure 11E:
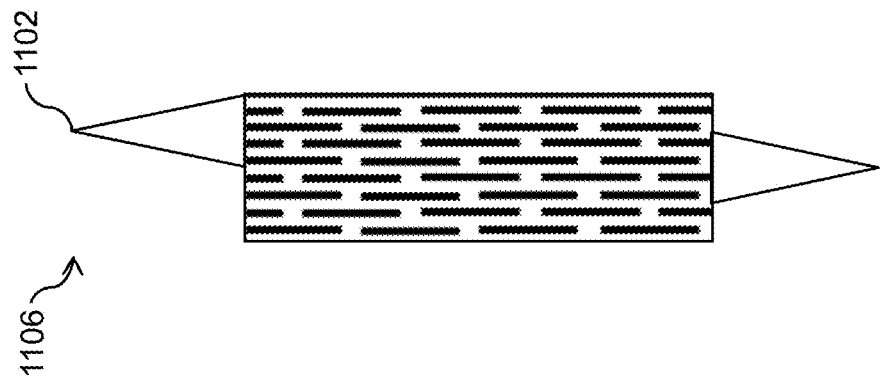
FIGS. 11D-E are diagrammatic top plan views of layers of thin-film micromesh that join at the edges to form the thin-film micromesh of FIG. 11C when expanded to its three-dimensional form according to an embodiment.
Figure 11D:
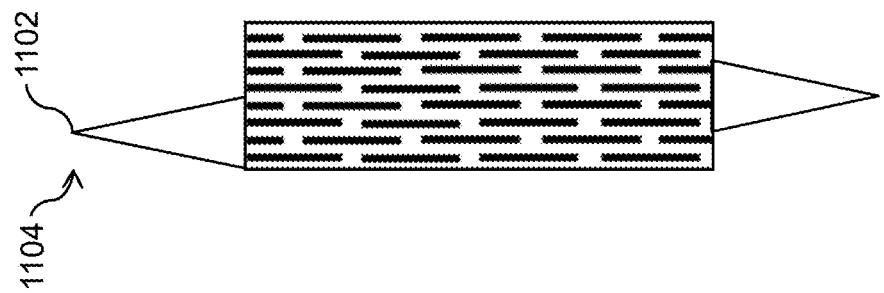
Figure 11C:
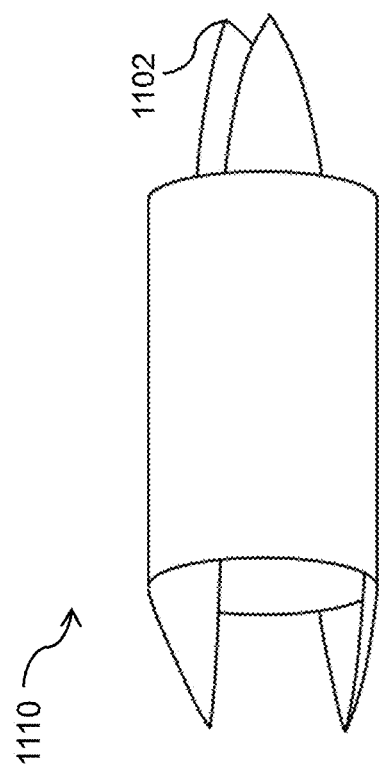
FIG. 11C is a diagrammatic side elevational view of a thin-film micromesh with attachment points/areas on one end staggered from attachment points/areas on an opposing end according to an embodiment.

FIG. 11C shows a side elevational view of thin-film mesh 1110 expanded to its three-dimensional form with attachment points/areas on one end staggered from attachment points/areas on an opposing end. Thin-film mesh 1110 may include two attachment points 1102 at one end and two additional attachment points 1102 at the opposing end. Attachment points 1102 at one end may be rotated 90 degrees relative to the attachment points 1102 at the opposing end.

Thin-film mesh 1110 having two attachment points 1102 at each end rotated 90 degrees relative to each other as shown in FIG. 11C may be formed by depositing a Nitinol layer 1104 shown in FIG. 11D on an etched wafer (e.g., Nitinol layer 410 on etched wafer 400 as shown in FIGS. 4G and 5D) as described above with respect to block 306 of FIG. 3, depositing a sacrificial layer (e.g., sacrificial layer 422 as shown in FIGS. 4L and 5E) on Nitinol layer 1122 as described above with respect to block 316 of FIG. 3, and then depositing a Nitinol layer 1126 shown in FIG. 11E (e.g., Nitinol layer 424 as shown in FIGS. 4N and 5F) on the sacrificial layer 224 and edges of Nitinol layer 1122 as described above with respect to block 320 of FIG. 3. Alternatively, Nitinol layer 1122 and Nitinol layer 1126 may be fabricated on separate wafers and joined at the long/longitudinal edges thereafter.

FIG. 11F is a diagrammatic side elevational view of thin-film mesh device 1120 including thin-film mesh 1110 attached to backbone 122 at one or more attachment points/areas 1102. Attachment using one or more attachment points/areas 1102 advantageously confers flexibility to thin-film mesh device 1120. Because blood vessels in the body are often curved and not straight, thin-film mesh device 1120 may be bent around a curvature of a blood vessel. The problem of keeping thin-film mesh 1110 in place on backbone 122 when thin-film mesh device 1120 is bent in tortuous blood vessels is resolved by attaching thin-film mesh 1110 that is flexible to stent backbone 122/722 using attachment points/areas 1102.

As shown in FIG. 11G, when thin-film mesh device 1120 is bent, thin-film mesh 1110 is held in place by attachment points/areas 1102. Thin-film mesh 1110 may have an angle 1122 at or near attachment point 1102 when not bent around a curve (as shown in FIG. 11F) and an angle 1124 smaller than angle 1122 at or near attachment point 1102 when thin-film mesh 1110 is bent around a curve (as shown in FIG. 11G) as thin-film mesh 1110 is expanded longitudinally along backbone 122 and narrowed laterally due to the curvature. The state of expansion of thin-film mesh 1110 in FIG. 11G may be an intermediate expanded state, which may be in between thin-film mesh 1100 as shown in FIG. 11A (unexpanded state) and thin-film mesh 1110 as shown in FIG. 11B (fully expanded state).

Figure 12D:
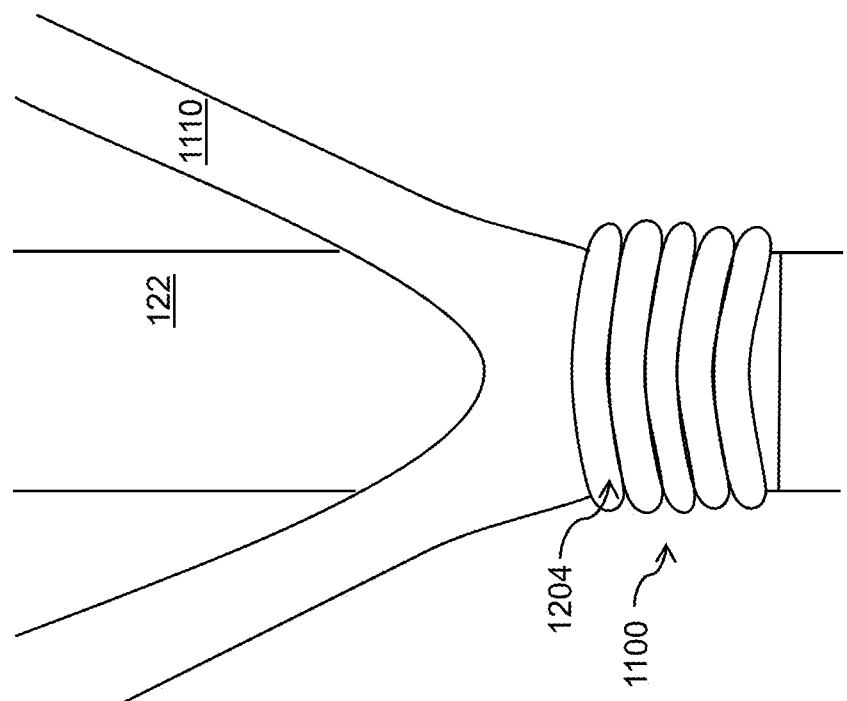
FIGS. 12C-D are diagrammatic close-up views of an attachment point/area with a wrapping area according to an embodiment.
Figure 12C:
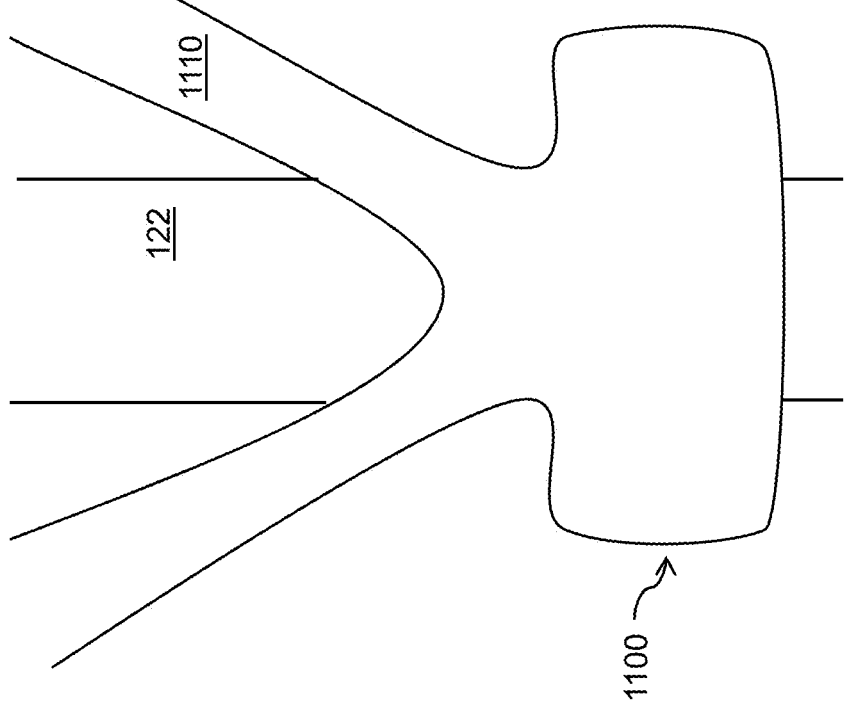

FIGS. 12A-D show diagrammatic close-up views of attachment points/areas 1102 of thin-film meshes 1110. In some embodiments, attachment point/area 1102 includes two holes 1202 at attachment point/area 1102 as shown in FIG. 12A. Thin-film mesh 1110 may be attached to backbone 122 at attachment point/area 1102 using a wire or thread 1204 that is placed through holes 1202 and around backbone 122, as shown in FIG. 12B. Wire or thread 1204 may be a metal wire, such as a gold wire that may also function as a radiopaque marker, or a polymer thread, such as polymer threads used for sutures. In other embodiments, attachment point/area 1102 may be an area for wrapping around backbone 122 as shown in FIG. 12C. Wire or thread 1204 may be used to wrap around attachment point/area 1102 as shown in FIG. 12D. In further embodiments, a solder may be used to attach thin-film mesh 1110 onto backbone 122.

Figure 13B:
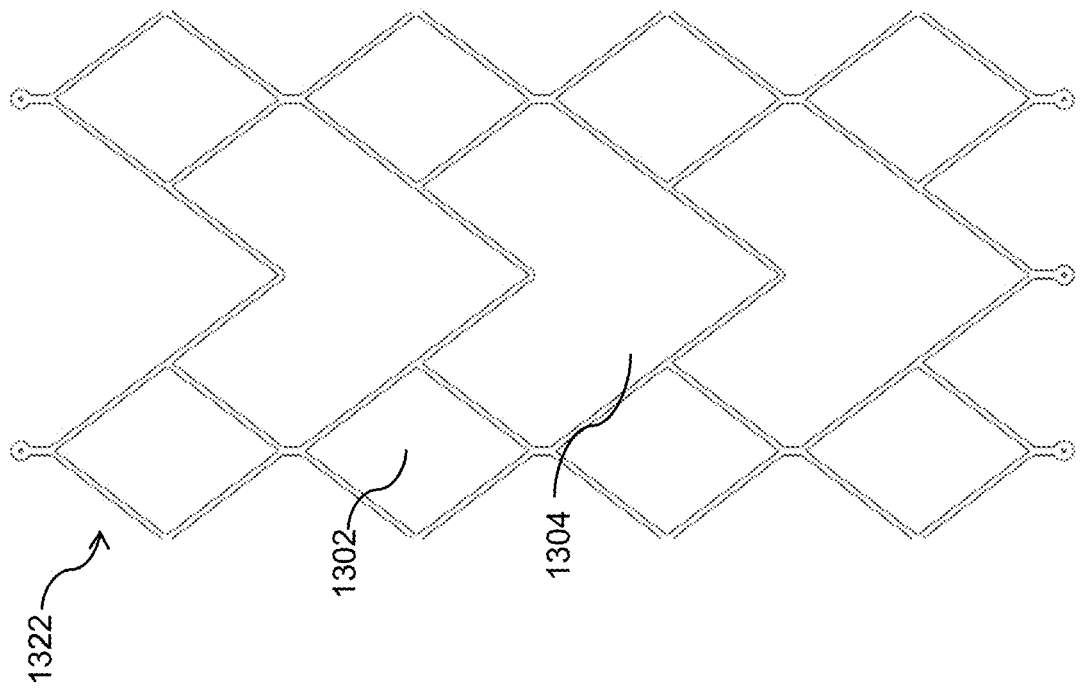
FIGS. 13A-B are diagrammatic flat-pattern views of portions of kink-resistant stent backbones including V-shaped/heart-shaped fenestrations according to one or more embodiments.
Figure 13A:
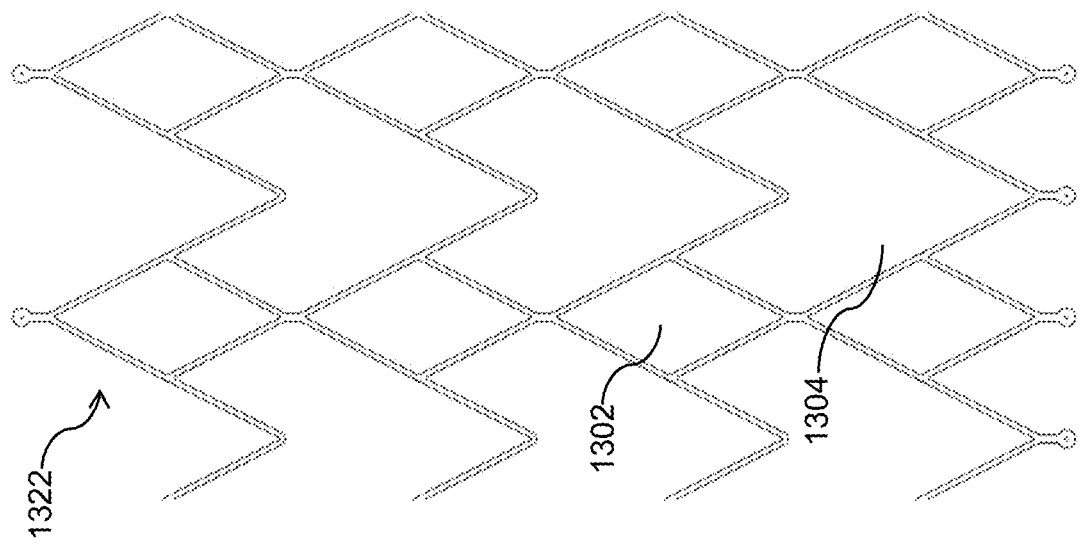

FIGS. 13A-B are diagrammatic flat-pattern views of kink-resistant stent backbones 1322 (e.g., backbone 122 in FIGS. 1C-1D and 2D). Flat pattern views are how stent backbones 1322 would look if sliced along the longitudinal direction and opened flattened (i.e., in its three-dimensional cylindrical form, the left ends are joined to the right ends). Stent backbones 1322 have "chain-link" fence patterns including diamond-shaped fenestrations 1302 and heart-shaped/V-shaped fenestrations 1304. It will be appreciated that stent backbones 1322 including fenestrations of other shapes may be used in alternative embodiments. A thin-film mesh device (e.g., thin-film mesh device 120 in FIG. 1C) that includes a thin-film mesh (e.g., thin-film mesh 110 in FIG. 1B) attached to stent backbone 1322 is advantageously kink-resistant and flexible. Accordingly, kink-resistant stent backbone 1322 may be structured to optimally interact with thin-film mesh 110 and further utilize the advantageous features of thin-film mesh 110.

Figure 14:
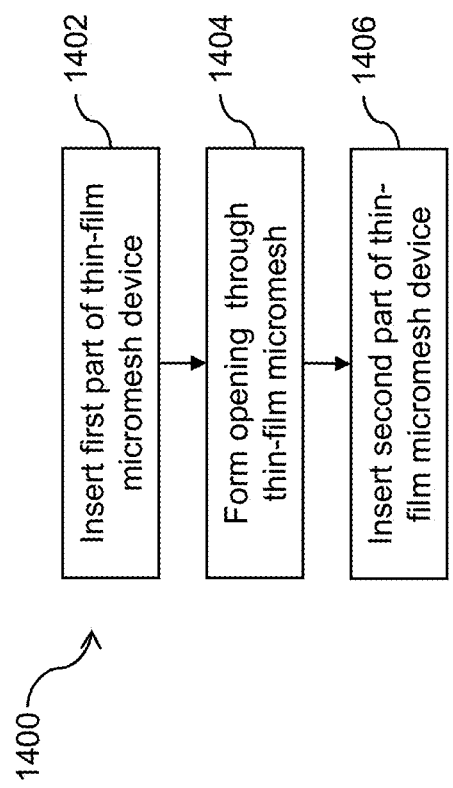
FIG. 14 is a flow diagram of a process to implant a modular thin-film micromesh stent at a bifurcated aneurysm site according to an embodiment.
Figure 15A:
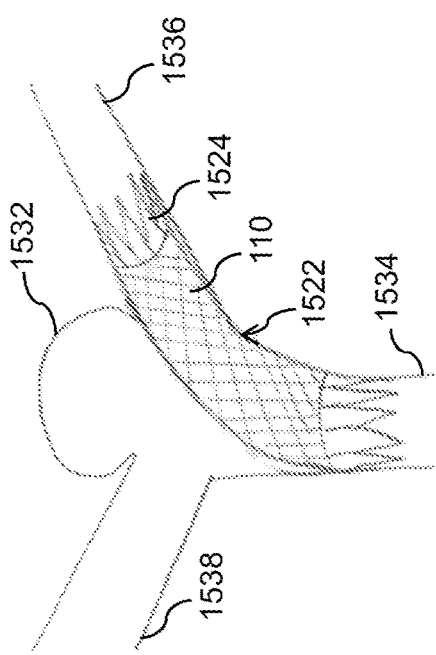
FIGS. 15A-C are diagrammatic cross-sectional views of a bifurcated aneurysm site in which a modular thin-film micromesh stent is implanted according to an embodiment.
Figure 15B:
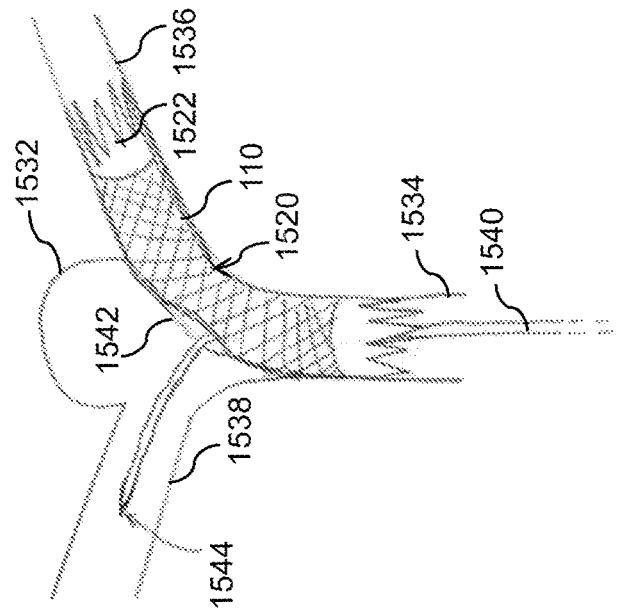
Figure 15C:
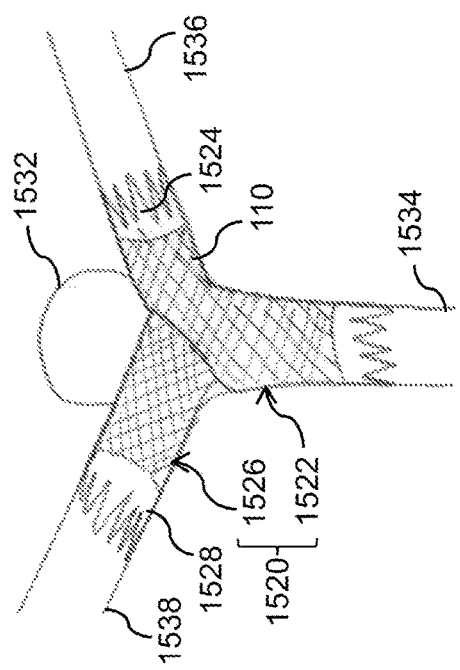

FIG. 14 is a flow diagram of a process 1400 to insert a modular thin-film mesh stent device 1520 including at least two thin-film mesh stent modules 1522, 1526 at a site including a bifurcated aneurysm 1532 (e.g., an intracranial aneurysm at a vessel bifurcation) as shown in FIGS. 15A-C. At block 1402, thin-film mesh stent module 1522 is inserted such that it extends from blood vessel 1534 to one side of bifurcation such as blood vessel 1536, as shown in FIG. 15A. Thin-film mesh stent module 1522 may include thin-film mesh 110 over a stent backbone 1524. Stent backbone 1524 may have a low percent metal coverage (e.g., approximately 8% or less). Stent backbone 1524 may be designed with fenestrations that are large and open to accommodate modular stenting. Alternatively, stent backbone 1524 may be designed with a large open section or hole in the middle to accommodate modular stenting.

At block 1404, a penetrating wire 1540 is used to make a hole/opening 1542 in thin-film mesh 110 on thin-film mesh stent module 1522, as shown in FIG. 15B. Penetrating wire 1540 may be configured to facilitate smooth penetration of thin-film mesh 110. For example, penetrating wire 1540 may have a tip 1544 that is sharp or a barbed structure close to tip 1544.

At block 1406, thin-film mesh stent module 1526 may be placed through hole 1542 on thin-film mesh stent module 1522 such that it extends from blood vessel 1534 to the other side of bifurcation such as blood vessel 1538, as shown in FIG. 15C. Thin-film mesh stent module 1526 may include thin-film mesh 110 over a stent backbone 1528. Thin-film mesh stent module 1526 may be configured to effectively interact with thin-film mesh stent module 1522. For example, thin-film mesh stent module 1526 may be tapered or flared at one or both ends to fit hole/opening 1542 on thin-film mesh stent module 1522. In another example, stent backbone 1528 may only be partially covered with thin-film mesh 110 (e.g., the distal portion of stent backbone 1528) so that the portion of thin-film mesh stent module 1526 inside thin-film mesh stent module 1522 is not covered with thin-film mesh 110 to avoid overlap of thin-film mesh 110.

Treating bifurcated aneurysm 1532 using modular thin-film mesh stent device 1520 avoids problems faced in conventional techniques. For example, conventional Y-stenting techniques are unsatisfactory because they involve placing two stents in a single parent vessel. Further, intrasaccular therapies that involve placing a spherical mesh structure inside an aneurysm have numerous disadvantages, such as the spherical mesh being difficult to size properly and requiring a physician to enter and manipulate the fragile aneurysm sac. Modular thin-film mesh stent device 1520 is a more effective device, as it does not require placing two stents in the parent vessel—there is only one opening at blood vessel 1534 once modular thin-film mesh stent device 1520 is formed by combing two modules 1522 and 1526, and modular thin-film mesh stent device 1520 does not require sizing or manipulating of the fragile aneurysm sac.

FIGS. 16A-E show illustrative micropatterned shapes (e.g., fractal, fractal-like, or other complex micropatterns) that may be implemented as pore edges or pore shapes for pores/fenestrations (e.g., pores/fenestrations 112) of a thin-film mesh such as thin-film mesh 110. A challenge in tissue engineering is establishing a three-dimensional structure in a desired shape that can serve as a scaffold for cellular in-growth. Thin-film mesh 110 (e.g., a TFN mesh) can serve as such a material by (1) being covered with a fibrinous layer derived from blood products (including fibrin and platelets) when placed in flowing blood and (2) by the in-growth of endothelial cells from adjacent endogenous tissue (seeding process). The ability of the cells to grow onto this fibrinous layer and for the layer to be formed depends upon particular characteristics of thin-film mesh 110. When blood is flowing over or through a piece of thin-film mesh 110 that has porosities patterned into it, a greater cumulative edge length of the pores leads to greater cellular in-growth.

In one or more embodiments, pores are formed with fractal micropatterns to provide maximized edge length while minimizing any reduction in the pore area. Conventionally, pores have been patterned with simple geometries, such as squares or parallelograms. Fractals are geometric shapes that exhibit the property of self-similarity at different scales; examples include the Koch Snowflake, Gosper Island, and Sierpinski sieve. In contrast to the simpler geometric patterns previously employed, there is a clear advantage to using pores that employ complex, fractal, or fractal-like micropatterning of thin-film mesh 110. These geometries serve to advantageously increase the edge length of the pores, as the cumulative edge length per unit of area is a determinant of successful deposition of a fibrinous layer and the growth of a physiologic-like layer of cells.

Figure 16E:
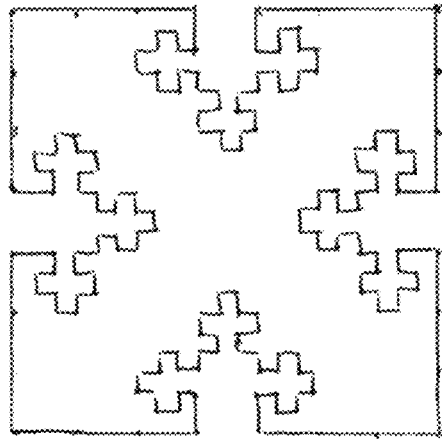
FIGS. 16A-E illustrate shapes that may be implemented as pore edges or pore shapes of a thin-film micromesh according to one or more embodiments.
Figure 16C:
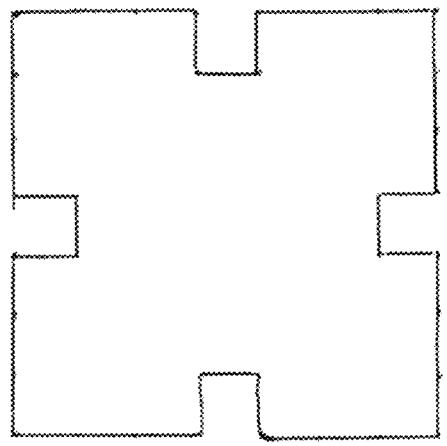
Figure 16D:
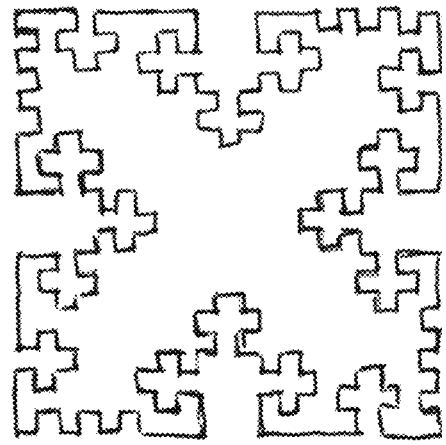
Figure 16A:
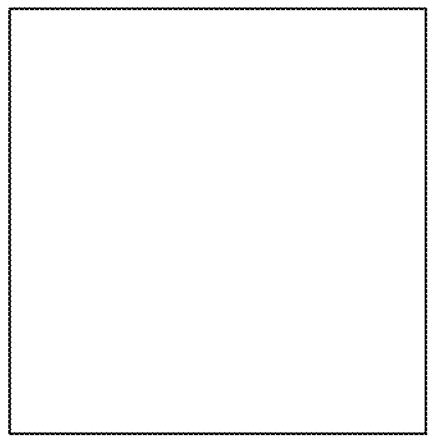
Figure 16B:
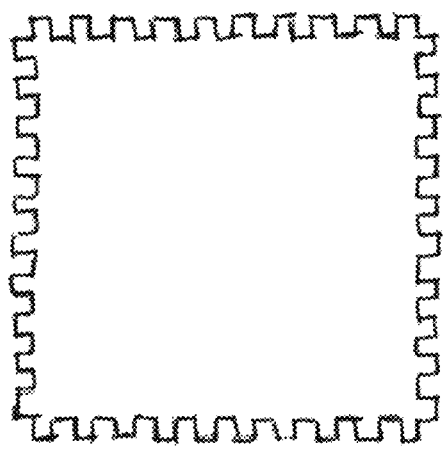

The pore edges (e.g., the struts formed by thin-film mesh 110 around each pore) of thin-film mesh 110 may have no complex, fractal, or fractal-like micropatterns as shown in FIG. 16A, or may have complex, fractal, or fractal-like micropatterns as shown in FIGS. 16B-E. These are intended to be examples, and other specific configurations may be apparent to one skilled in the art. In FIG. 16A, the pore is a simple square shape with straight line edges. In FIG. 16B, the edges of the pore have been made more complex with dentaling or tooth-like modifications, which increases edge length. In FIG. 16C, a simple fractal-generation rule has been applied, in that the middle section of each line segment is displaced into the central area of the pore, which also increases edge length. FIGS. 16D and 16E are example refinements of the pores in FIGS. 16B and 16C, with the patterns becoming increasingly complex and the edge length increased. Different applications may be best suited by different balances between increases in edge length and decreases in pore area. Examples of values for FIGS. 16A-E are shown in the table below.

above with respect to block 302 of FIG. 3. Using the etched wafer, the thin-film mesh cover with the complex, fractal, or fractal-like micropatterned pores may be formed as described above with respect to blocks 304-326 of FIG. 3. The micropatterned thin-film mesh may or may not require expanding to open up fenestrations as described above with respect to block 328 of FIG. 3 depending on whether the fenestrations are fabricated as slits to be opened up or as pores that do not require expansion. Micropatterned thin-film mesh 110 may be shaped to its three-dimensional form (e.g., a cylindrical tube) and then assembled on a backbone or a scaffold (e.g., a stent backbone) such as backbone 122. The characteristics of the micropattern may be selected to ensure the correct balance between edge length and pore area, and to ensure providing the appropriate elasticity to thin-film mesh 110. The complex, fractal, or fractal-like geometry provides greater edge length for each pore with little or no reduction in pore size. Advantageously, the greater edge length promotes fibrin binding and cell growth (e.g., endothelialization) while still allowing blood flow through the pore, as the pore size is not significantly reduced.

Figure 17:
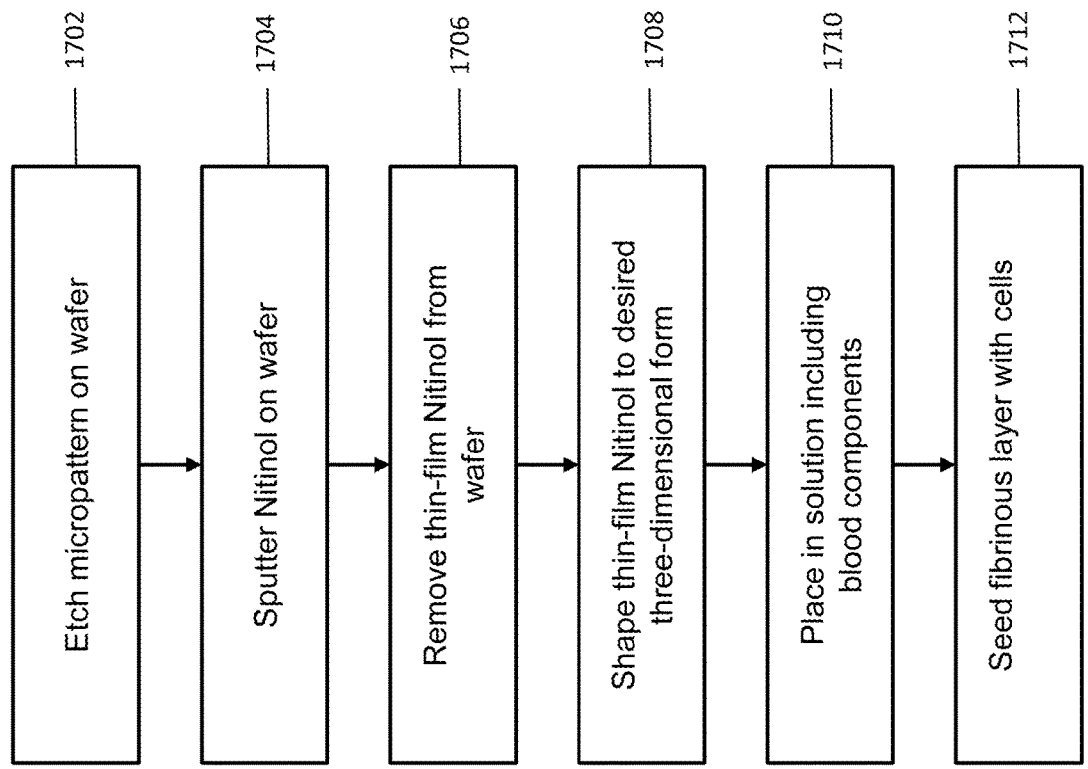
FIG. 17 is a flow diagram of a process to fabricate a thin-film micromesh for a medical device for a tissue-engineering according to one or more embodiments.

FIG. 17 shows a flow diagram of a process to fabricate a thin-film mesh such as thin-film mesh 110 for a thin-film mesh device (e.g., a thin-film mesh scaffold device) such as thin-film mesh device 120 for tissue-engineering. Thin-film mesh device 120 may be composed of or include thin-film mesh 110 that is a thin-film mesh membrane (e.g., a TFN membrane), a three-dimensional (3D) thin-film mesh structure (e.g., a 3D TFN structure), or other thin-film mesh structure. In some embodiments, thin-film mesh 110 may have diamond-shaped pores as shown in FIG. 1B or 7A-C. In some embodiments, thin-film mesh 110 may include pores with complex, fractal, or fractal-like pre edges or pore shapes as shown in FIGS. 11B-E.

At block 1702 a micropattern is etched on a wafer (e.g., as described in relation to block 302 of FIG. 3). In some embodiments, a complex, fractal, or fractal-like micropattern according to FIGS. 11B-E is etched on the wafer. For example, grooves or trenches (e.g., trenches 406 in FIG. 4E or 5C) may be etched according to the complex, fractal, or fractal-like micropattern using a deep reactive ion etching (DRIE) process.

At block 1704, a layer of Nitinol (e.g., e.g., Nitinol layer 410 as shown in FIGS. 4G and 5D) is sputter-deposited on the wafer to form a thin-film mesh on the wafer (e.g., as described with respect to block 306 of FIG. 3). In some embodiments, one or more sacrificial layers (e.g., sacrificial layer 422 as shown in FIGS. 4L and 5E) and one or more additional layers of Nitinol (e.g., Nitinol layer 424 as shown

| Configuration: | FIG. 16A | FIG. 16B | FIG. 16C | FIG. 16D | FIG. 16E |
|---|---|---|---|---|---|
| Area | 441 | 401 | 405 | 301 | 333 |
| Normalized Area | 1.000 | 0.909 | 0.918 | 0.683 | 0.755 |
| Edge Length | 84 | 156 | 108 | 300 | 236 |
| Normalized Edge Length | 1.000 | 1.857 | 1.286 | 3.571 | 2.810 |
| Normalized Edge Length/ Normalized Area | 1.000 | 2.042 | 1.400 | 5.233 | 3.721 |

In some embodiments, thin-film mesh 110 with complex, fractal, or fractal-like micropatterned pores may be used as a thin-film mesh cover for a stent device. A complex, fractal, or fractal-like micropattern may be etched on a silicon wafer. For example, grooves or trenches (e.g., trenches 406 in FIG. 4E or 5C) may be etched on the wafer according to the complex, fractal, or fractal-like micropattern as described in FIGS. 4N and 5F) may be deposited (e.g., as described above with respect to block 316 and block 320 in FIG. 3) depending on the three-dimensional shape of thin-film mesh 110 that is desired. In some embodiments, the layer of Nitinol is sputter-deposited on the complex, fractal, or fractal-like micropatterned grooves of the wafer. The complex, fractal, or fractal-like micropattern of grooves is duplicated on the resulting thin-film mesh as complex, fractal, or fractal-like micropatterned fenestrations.

At block 1706, the thin-film mesh is removed from the wafer (e.g., as described with respect to block 326 in FIG. 3).

At block 1708, macroscopic features are created by shaping thin-film mesh 110 to the desired form to form thin-film mesh device 120 to serve as a scaffold for tissue engineering. Thin-film mesh 110 may be shaped via stamping, wrapping thin-film mesh 110 over a forming apparatus (e.g., a mold), or vacuum forming over a forming apparatus with a layer of plastic placed over thin-film mesh scaffold 110. In some embodiments, thin-film mesh device 120 further includes a backbone such as backbone 122 for support or to deliver thin-film mesh 110.

At block 1710, the shaped thin-film mesh scaffold 110 is removed from the forming apparatus and extracellular matrix components (e.g., collagen, elastin, fibronectin, laminin, and/or other extracellular matrix components) or other biomolecules may be provided on thin-film mesh scaffold device 120. Thin-film mesh scaffold device 120 is thereby configured to promote cell growth while simultaneously achieving advantageous mechanical properties and allowing for cell migration and exchange of nutrients and information.

In one or more embodiments, thin-film mesh scaffold device 120 is placed in a fluid (e.g., a solution including extracellular matrix components or other biomolecules) such that a fibrinous layer of coagulated material is deposited on thin-film mesh 110. In an example, the fluid may be a blood-based fluid such as blood plasma, blood serum, or other blood-based fluid. The fluid may contain fibrin, fibrinogen, clotting factors, and/or other components of whole blood, but may exclude red blood cells and white blood cells. In some embodiments, the fluid may be passed over thin-film mesh scaffold device 120 to deposit the fibrinous layer of coagulated materials. In other embodiments, thin-film mesh scaffold device 120 is coated with extracellular matrix components or other biomolecules.

At block 1712, the fibrinous layer on thin-film mesh scaffold device 120 is seeded with cells selected to be compatible with the individual for whom the engineered tissue is being prepared. For example, the fibrinous layer may be seeded with epithelial cells, endothelial cells, or stem cells (e.g., pluripotent stem cells). Thin-film mesh scaffold device 120 may then be bathed in a fluid containing growth factors selected to match the cells that were seeded and induce the cells to grow into the type of tissue desired.

Thin-film mesh scaffold device 120 formed via blocks 1702-1712 is a particularly advantageous platform for tissue engineering and cell growth. Thin-film mesh scaffold device 120 may have pores of any shape with a pore size between 1 mm and 5 µm, or even less using more advanced lithography techniques such as electron beam writing. Such pores allow for intercellular communication, nutrient exchange, fluid flow, and movement. Thin-film mesh scaffold device 120 is strong and at the same time malleable, in contrast to conventional cell scaffold devices composed of or including hydrogels, fibrin based gels, and electrospun polymers that are too brittle or too malleable. Thus, conventional cell scaffold devices fail to achieve the desired conformation, strength, and controlled porosity of thin-film mesh scaffold device 120. Moreover, conventional scaffold devices also suffer from the inability to engineer exact pore configurations and instead rely on a random distribution of pores. Further, thin-film scaffold device 120 may be composed of or include TFN which, as a shape memory alloy, returns to its formed shape even after significant mechanical distortion. Gels, polymers, and most other materials do not share this property.

In some embodiments, thin-film mesh scaffold device 120 may be used in conjunction with biological substrates to facilitate rapid cellular in-growth of the tissue engineering construct. Thin-film mesh scaffold device 120 with the addition of biological substrates may be referred to as a hybrid scaffold or hybrid membrane. For example, thin-film mesh scaffold device 120 may be incubated with whole blood, plasma, platelet rich plasma, platelet rich fibrin, platelet poor fibrin, collagen solutions, or solutions of other extracellular matrix proteins to create a hybrid scaffold, which may be used for cell growth and tissue engineering. The biological components of the hybrid scaffold facilitate rapid cellular ingrowth of the construct (either in vitro or in vivo) while thin-film mesh 110 and/or backbone 122 provides the structure for tissue ingrowth and interaction between cells on the construct or with cells of the host organism receiving the construct.

In some embodiments, thin-film mesh scaffold device 120 may be annealed in the desired anatomical configuration prior to seeding with the biological components. As thin-film mesh scaffold device 120 is exceptionally malleable, thin-film mesh scaffold device 120 may be annealed in virtually any shape to facilitate interaction with the host tissue and/or to position cells in advantageous configurations that will facilitate intercellular interactions. Because of the shape memory properties of thin-film mesh scaffold device 120, it will return to the given shape even after forces transiently distort it.

Figure 18:
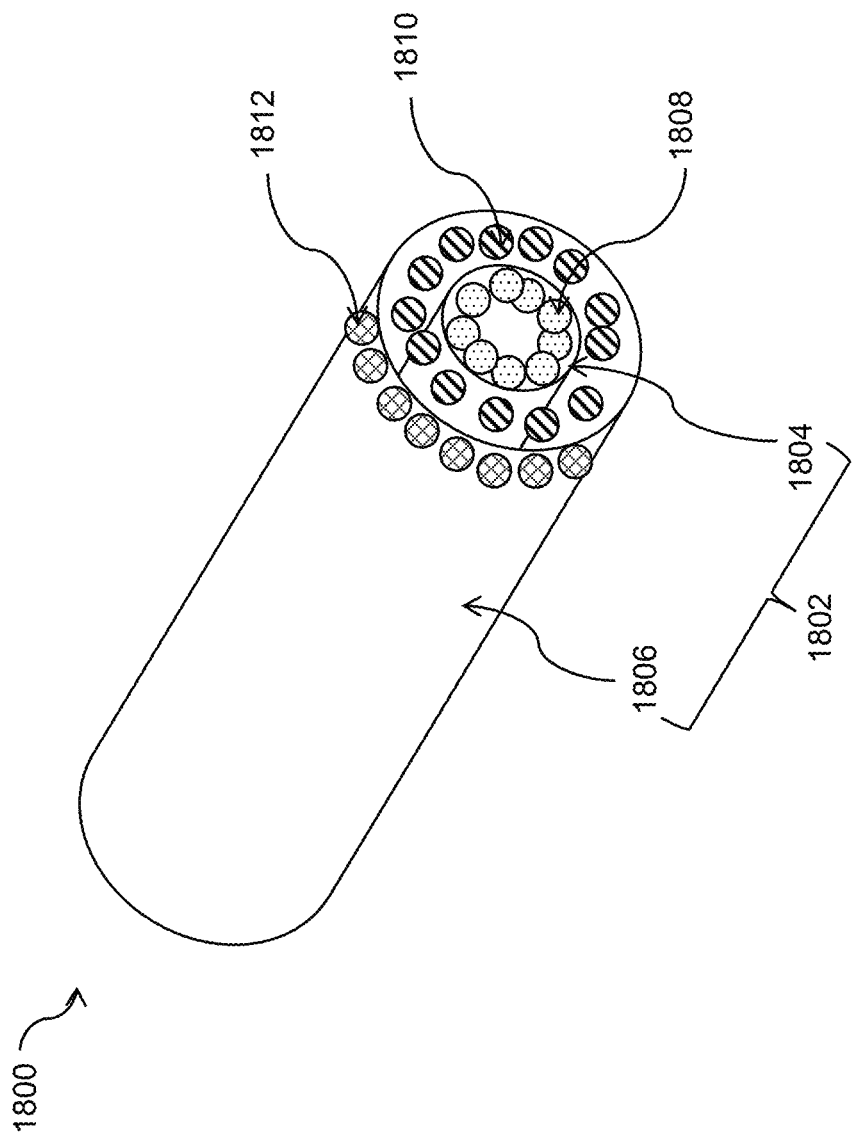
FIG. 18 is a diagrammatic perspective view of a multi-layered thin-film micromesh membrane for a tissue engineered vascular graft (TEVG) according to an embodiment.

FIG. 18 is a diagrammatic perspective view of a multi-layered thin-film mesh membrane 1802 that may be used, for example, to create a tissue engineered vascular graft (TEVG) 1800. Multi-layered thin-film mesh membrane 1802 may include an inner thin-film mesh cylinder 1804 and an outer thin-film mesh cylinder 1806. Multi-layered thin-film mesh membrane 1802 may further include one or more intermediate thin-film mesh cylinders (not shown in FIG. 18). Inner thin-film mesh cylinder 1804 includes a tubular micropatterned thin-film mesh, which may have mechanical properties similar to the inner elastic layer of a vessel wall (e.g., the internal elastic lamina). Outer thin-film mesh cylinder 1806 includes another tubular micropatterned thin-film mesh, which may have mechanical properties that are similar to the outer elastic layer of a vessel wall (e.g., the external elastic lamina). Inner thin-film mesh cylinder 1804 and outer thin-film mesh cylinder 1806 may be formed, for example, using the process described above with respect to FIG. 3.

Inner thin-film mesh cylinder 1804 and outer thin-film mesh cylinder 1806 may be incubated with biomolecules to form hybrid inner and outer membranes prior to, or concurrently with, seeding cells. Endothelial cells 1808 may be seeded on inner thin-film mesh cylinder 1804 (e.g., on the inner surface, the outer surface, or both), which may grow to generate a layer of endothelial cells (e.g., the tunica intima of a vessel). Smooth muscle cells 1810 may be seeded between inner thin-film mesh cylinder 1804 and outer thin-film mesh cylinder 1806, which may grow to generate smooth muscle tissue (e.g., the tunica media of a vessel). Fibroblast cells 1812 may be seeded on the outer thin-film mesh cylinder 1806 (e.g., on the inner surface, the outer surface, or both), which may grow to generate connective tissue (e.g., the adventitia of a vessel). The seeded multi-layered thin-film mesh membrane 1802 may be incubated to grow the cells and used during a vascular graft procedure on a patient.

FIGS. 19A-B show a double-spiral thin-film mesh membrane 1900 and a 3D double-spiral thin-film mesh structure 1910. As shown in FIG. 19A, double-spiral thin-film mesh membrane 1900 may be flat or substantially flat. Alternatively, double-spiral thin-film mesh membrane 1900 may be formed to have a curved shape (e.g., to conform to the shape of a part of the body). Double-spiral thin-film mesh membrane 1900 may be made from a layer of thin-film mesh deposited on a silicon wafer. For example, grooves may be etched on a silicon wafer according to a double-spiral shape, a layer of thin-film mesh may be deposited in the grooves of the wafer to form the double-spiral thin-film mesh membrane 1900, and then the double-spiral thin-film mesh membrane 1900 may be removed from the wafer using a lift-off process (e.g., as described above with respect to process 300 in FIG. 3 and process 1700 in FIG. 17).

As shown in FIG. 19B, 3D double-spiral thin-film mesh structure 1910 includes a plurality of double-spiral thin-film mesh membranes 1900 stacked to create a three-dimensional cell matrix. In some embodiments, 3D double-spiral thin-film mesh structure 1910 may be formed from a plurality of double-spiral thin-film mesh membranes 1900 formed with a single layer of thin-film mesh on a wafer. In other embodiments, 3D double-spiral thin-film mesh structure 1910 may be formed by depositing multiple layers of thin-film mesh on a wafer separated by multiple layers of sacrificial layers (e.g., as described above with respect to process 300 in FIG. 3).

In some embodiments, each of double-spiral thin-film mesh membranes 1900 may include a plurality of struts 1902 sized to facilitate cell growth. The struts of 3D double-spiral thin-film mesh structure 1910 may have a density to facilitate cell growth and provide similar structural and/or mechanical properties as a tissue in the body.

In some embodiments, each of double-spiral thin-film mesh membrane 1900 may include a central opening 1904 that foul's a central channel 1906 through which fluid may flow. For example, a fluid with nutrients may flow through central channel 1906 and provide nutrients to cells growing in or on 3D double-spiral thin-film mesh structure 1910.

In an example, 3D double-spiral thin-film mesh structure 1910 may be used as a scaffold device for growing a part of a bone, such as an osteon. 3D double-spiral thin-film mesh structure 1910 may be incubated with biomolecules to form a hybrid structure prior to, or concurrently with, seeding cells. Bone cells (e.g., osteoblasts, osteoclasts, etc.) may be seeded in 3D double-spiral thin-film mesh structure 1910, which may grow and deposit calcium to form the osteon. 3D double-spiral thin-film mesh structure 1910 may be used during a bone graft procedure on a patient.

Figures 20A, 20B:
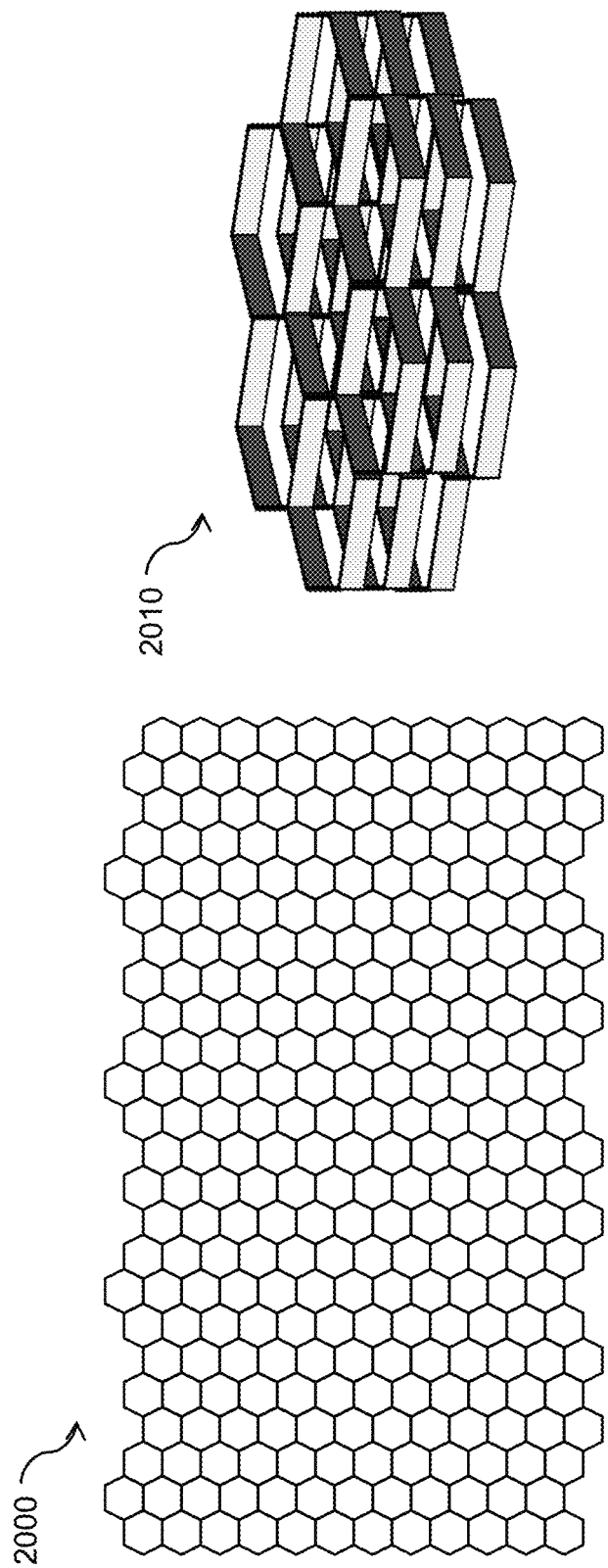
FIG. 20A is a diagrammatic top plan view of a honey-comb thin-film micromesh membrane according to an embodiment.
FIG. 20B is a diagrammatic perspective view of a three-dimensional honeycomb thin-film micromesh structure according to an embodiment.

FIGS. 20A-B show a honeycomb thin-film mesh membrane 2000 and a 3D honeycomb thin-film mesh structure 2010. As shown in FIG. 20A, honeycomb thin-film mesh membrane 2000 may be flat or substantially flat. Alternatively, honeycomb thin-film mesh membrane 2000 may be formed to have a curved shape (e.g., to conform to the shape of a part of the body). Honeycomb thin-film mesh membrane 2000 may be made from a layer of thin-film mesh deposited on a silicon wafer. For example, grooves may be etched on a silicon wafer according to a honeycomb shape, a layer of thin-film mesh may be deposited in the grooves of the wafer to form honeycomb thin-film mesh membrane 2000, and honeycomb thin-film mesh membrane 2000 may then be removed from the wafer using a lift-off process (e.g., as described above in relation to process 300 in FIG. 3 and process 1700 in FIG. 17). Advantageously, due to the highly efficient packing of the honeycomb shape, honeycomb thin-film mesh membrane 2000 provides very low metal to surface area ratio and may be used to grow cells in a variety of tissue engineering applications.

In one example, honeycomb thin-film mesh membrane 2000 may be used for placement over wounds or damaged tissue. Honeycomb thin-film mesh membrane 2000 may be incubated with biomolecules (e.g., fibrin, collagen, growth factors, etc.) to form a hybrid membrane prior to, or concurrently with, seeding cells (e.g., stem cells). Honeycomb thin-film mesh membrane 2000 may then be placed over a wound or damaged tissue or wounds to facilitate healing.

As shown in FIG. 20B, 3D honeycomb thin-film mesh structure 2010 includes a plurality of honeycomb thin-film mesh membranes 2000 stacked to create a three-dimensional cell matrix. In some embodiments, 3D honeycomb thin-film mesh structure 2010 may be formed from 3D honeycomb thin-film mesh structure 2010 formed as a single layer of thin-film mesh on a wafer. In other embodiments, 3D honeycomb thin-film mesh structure 2010 may be formed by depositing multiple layers of thin-film mesh on a wafer separated by a sacrificial layer (e.g., as described above in relation to process 300 in FIG. 3).

In an example, 3D honeycomb thin-film mesh structure 2010 may be used as a scaffold device for guiding cell growth. 3D honeycomb thin-film mesh structure 2010 may be constructed to have a similar structure to a cross section of a nerve. 3D honeycomb thin-film mesh structure 2010 may be incubated with biomolecules to form a hybrid structure prior to, or concurrently with, seeding cells. 3D honeycomb thin-film mesh structure 2010 may be placed between two ends of a severed nerve to facilitate growth of nerve cells between the severed nerve.

Figure 21:
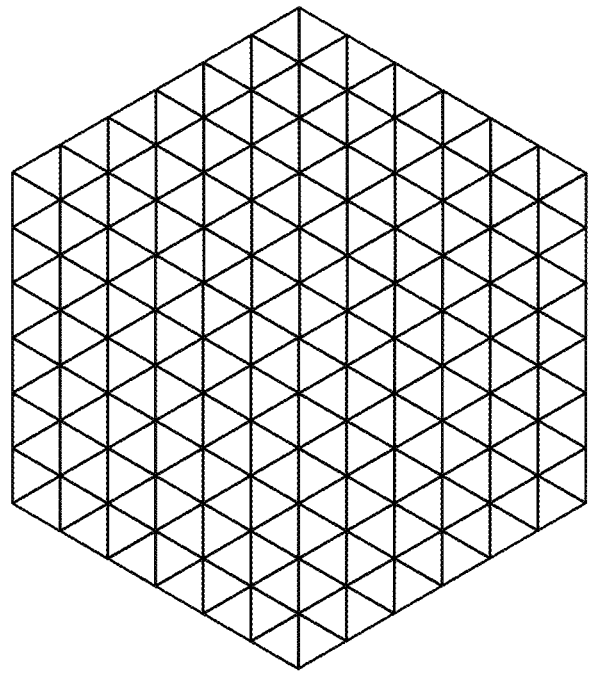
FIG. 21 is a diagrammatic top plan view of an equilateral-triangle thin-film micromesh membrane according to an embodiment.

FIG. 21 shows an equilateral-triangle thin-film mesh membrane 2100. Equilateral-triangle thin-film mesh membrane 2100 may be advantageously used for applications in which strong structural/mechanical properties are desirable.

Figure 22:
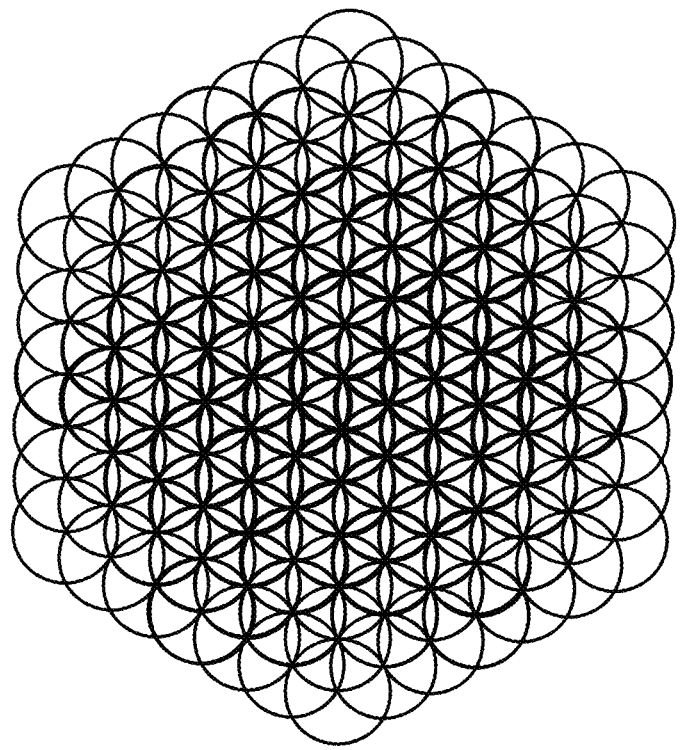
FIG. 22 is a diagrammatic top plan view of an overlapping-circle thin-film micromesh membrane according to an embodiment.

FIG. 22 shows an overlapping-circle thin-film mesh membrane 2200. Overlapping-circle thin-film mesh membrane 2200 may have dense connections, and may be advantageously used for applications in which strong structural/mechanical properties along with close packing of cells are desirable.

Figure 23B:
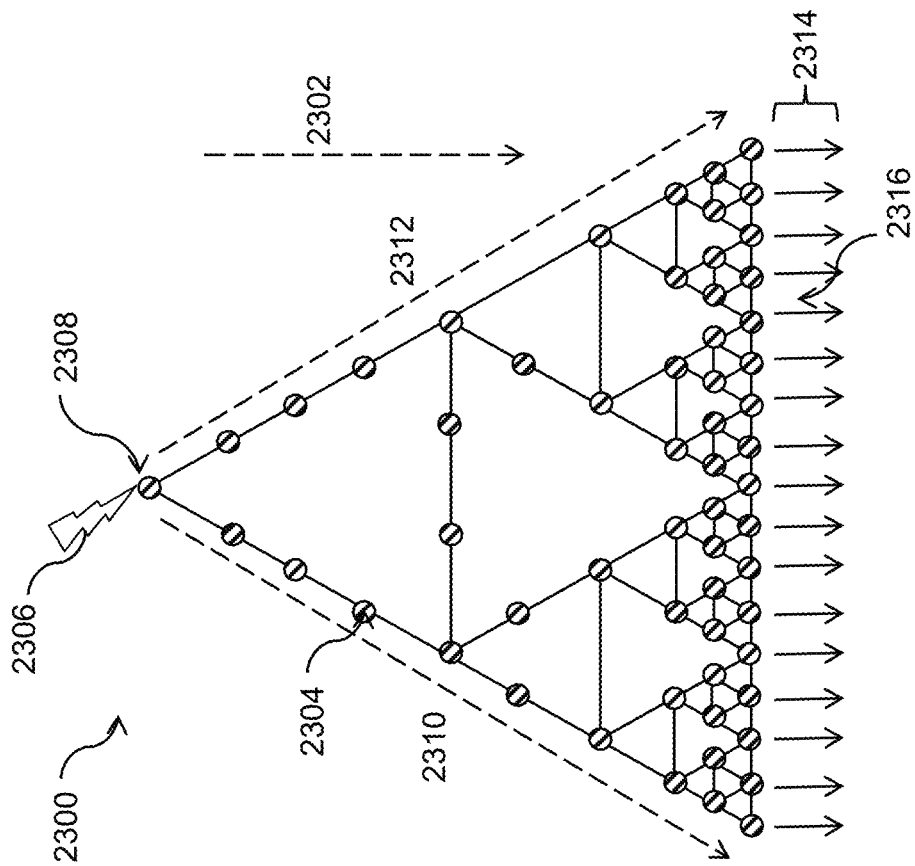
FIGS. 23A-B are diagrammatic top plan views of an amplifier thin-film micromesh membrane that is denser on one side/area according to an embodiment.
Figure 23A:
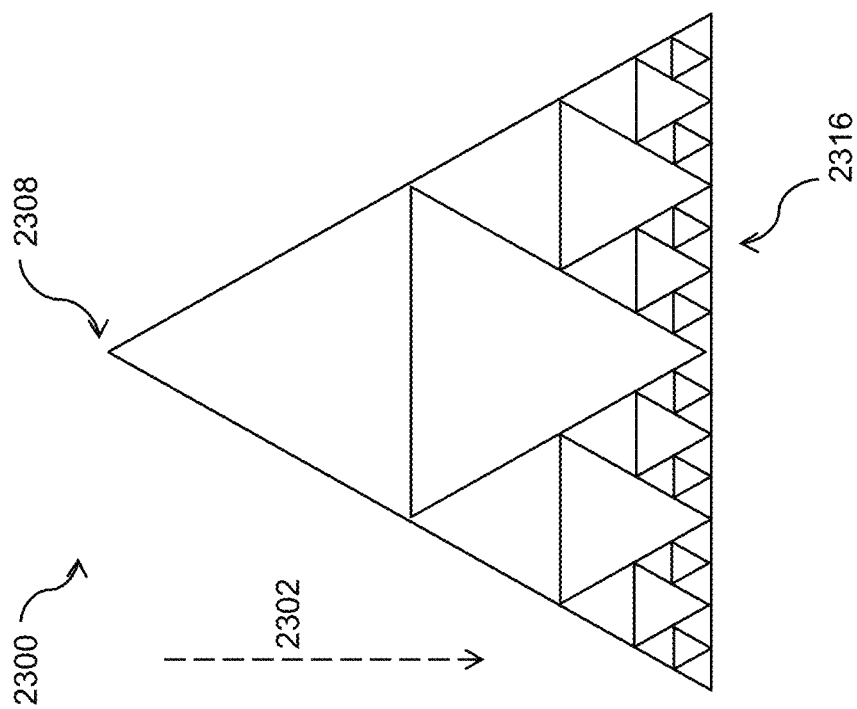

FIGS. 23A-B show an amplifier thin-film mesh membrane 2300 denser on one side/area (e.g., along direction 2302). Amplifier thin-film mesh membrane 2300 may be denser on one side/area by using fractal shapes or fractal-like shapes formed asymmetrically along direction 2302. Amplifier thin-film mesh membrane 2300 may be incubated with biomolecules (e.g., fibrin, collagen, growth factors, etc.) to form a hybrid membrane prior to, or concurrently with, seeding cells (e.g., neurons, muscle cells, cardiac myocytes). As shown in FIG. 23B, when cells 2304 are seeded on amplifier thin-film mesh membrane 2300, there may be progressively more cells 2304 when moving along direction 2302. Advantageously, cells 2304 may be grown and/or organized such that when stimulus 2306 is provided at one end 2308, one or more signals (e.g., neural signals) may be passed in direction 2302, for example via paths 2310, 2312, and paths in-between 2310 and 2312, thereby providing an amplified output 2314 at the other end 2316.

In various embodiments, flat or curved thin-film mesh membranes having other shapes may be formed to be used as a scaffold device for tissue engineering. Further, each of the flat thin-film mesh membranes may be stacked to create a 3D thin-film mesh structure that may be used as a 3D scaffold device for tissue engineering. The flat or curved thin-film mesh membranes and the 3D thin-film mesh structures may be seeded with cells to generate a cell matrix/construct, and grafted into a patient.

A thin-film mesh membrane (e.g., thin-film mesh membrane 1802, 1900, 2000, 2100, 2200, 2300, or other thin-film mesh membrane), a thin-film mesh structure (e.g., thin-film mesh structure 1910, 2010, or other thin-film mesh structure), or a corresponding hybrid membrane/structure may be used for various medical treatments as described below.

In some embodiments, a thin-film mesh membrane, a thin-film mesh structure, or a corresponding hybrid membrane/structure may be used, for example, for to facilitate wound healing for burns, pressure ulcers, scar revisions, ischemic lower limb ulcers and other acute and chronic wounds.

In some embodiments, a thin-film mesh membrane, a thin-film mesh structure, or a corresponding hybrid membrane/structure may be used to stop acute bleeding whether from injury or from surgical intervention ("hemostasis").

In some embodiments, a thin-film mesh membrane, a thin-film mesh structure, or a corresponding hybrid membrane/structure may be used to facilitate bone healing that is wrapped around or placed within a fracture site, or is wrapped around structural elements formed of other materials (e.g. titanium) that bridge a gap between bones.

In some embodiments, a thin-film mesh membrane, a thin-film mesh structure, or a corresponding hybrid membrane/structure may be used to grow human chondrocytes and create a thin plate of cartilage. This cartilage plate could be used in joint operations to delay knee or hip replacement or other osteoarthritic conditions.

In some embodiments, a thin-film mesh membrane, a thin-film mesh structure, or a corresponding hybrid membrane/structure may be used to deliver chemotherapeutics directly to the site of a tumor following surgical excision of the tumor.

In some embodiments, a thin-film mesh membrane, a thin-film mesh structure, or a corresponding hybrid membrane/structure may be used in cardiac surgery to place cardiac myocytes at a site of myocardial infarction. Following infarct the surgeon would excise the scarred area and insert the membrane or the hybrid membrane to facilitate regrowth of healthy tissue as opposed to scar tissue that typically accompanies myocardial infarction.

In some embodiments, a thin-film mesh membrane, a thin-film mesh structure, or a corresponding hybrid membrane/structure may be used as a scaffold device for nerve regrowth following injury. The thin-film mesh membrane or hybrid membrane would have channels aligned like a native nerve to facilitate axon growth in a controlled manner.

In some embodiments, a thin-film mesh membrane, a thin-film mesh structure, or a corresponding hybrid membrane/structure may be used in reconstructive or cosmetic surgery to replace ligaments because of the elastic properties of thin-film mesh (e.g., breast tissue contains multiple small ligamentous elements that give rise to the shape and mechanical properties of the organ, and post-mastectomy prostheses, i.e., breast implants, are essentially non-structured bags of saline, silicone gel, or other materials).

In some embodiments, thin-film mesh membranes, thin-film mesh structures, and/or corresponding hybrid membranes/structures can be joined together to create the basis for more complex cartilaginous structures (e.g., external ear, portions of nose) when seeded with chondrocytes.

In some embodiments, a thin-film mesh membrane, a thin-film mesh structure, or a corresponding hybrid membrane/structure may be used to replace elements of the eye that have been injured traumatically or by disease (e.g., a tumor).

In some embodiments, a thin-film mesh membrane, a thin-film mesh structure, or a corresponding hybrid membrane/structure may be used to construct replacement elements of the bronchial tree in the lungs.

In some embodiments, a thin-film mesh membrane, a thin-film mesh structure, or a corresponding hybrid membrane/structure composed of or including Nitinol may be seeded with myocytes to construct replacement skeletal muscle. Because Nitinol has the ability to change shape when electrical current is passed through it, it may be advantageously be used in artificial limbs.

In some embodiments, a thin-film mesh membrane, a thin-film mesh structure, or a corresponding hybrid membrane/structure may be used as a means to deliver both small and large molecules (i.e. proteins) to anatomical sites of interest.

Embodiments described herein illustrate but do not limit the disclosure. It should also be understood that numerous modifications and variations are possible in accordance with the principles of the present disclosure. Accordingly, the scope of the disclosure is best defined only by the following claims.

What is claimed is:

1. A thin-film micromesh device comprising:
    a metallic thin film formed from sputter deposition and etching on a substrate,
        wherein the etching is deep reactive ion etching (DRIE);
        wherein the metallic thin film has a length and includes a plurality of closed fenestrations, wherein the plurality of closed fenestrations are configured to become open fenestrations when the metallic thin film is expanded in a direction approximately perpendicular to the length,
        wherein the fenestrations form an overlapping-circle pattern, and
        wherein the metallic thin film is configured as a stent cover for a stent device;
    at least one of structural proteins, fibrin, collagen, elastin, fibronectin, laminin, or coagulated material formed on the metallic thin film; and
    a bioabsorbable backbone on which the metallic thin film is assembled, wherein the bioabsorbable backbone is configured to be absorbed after implantation in a patient for a predetermined amount of time.

2. The thin-film micromesh device of claim 1, wherein the metallic thin film or the structural proteins comprise one or more small molecules or large molecules configured to achieve a desired therapeutic effect at an anatomic site of interest where the thin-film micromesh device is to be deployed.

3. The thin-film micromesh device of claim 1, wherein the metallic thin film has a pore density of between 65 and 1075 pores per $mm^2$ and a percent metal coverage of between 16 and 66 when the metallic thin film is expanded to open up the plurality of fenestrations.

4. The thin-film micromesh device of claim 1, wherein the metallic thin film comprises thin-film Nitinol (TFN).

5. The thin-film micromesh device of claim 1, further comprising a plurality of metallic thin films each provided with structural proteins, wherein the plurality of metallic thin films are stacked together to form a three-dimensional thin-film micromesh structure.

6. The thin-film micromesh device of claim 1, further comprising an outer thin-film mesh cylinder enclosing an inner thin-film mesh cylinder, wherein each of the inner and the outer thin-film mesh cylinders is provided with structural proteins.

7. The thin-film micromesh device of claim 1, further comprising a seeded cell layer on the metallic thin film incubated to promote cell growth.

8. The thin-film micromesh device of claim 7, wherein the seeded cell layer comprises at least one of epithelial cells, endothelial cells, or stem cells.

9. The thin-film micromesh device of claim 1, wherein the metallic thin film has a percentage metal coverage of approximately between 6 to 83 percent.

10. The thin-film micromesh device of claim 1, wherein the structural proteins comprise growth factors.

* * * * *